US007908089B2

(12) United States Patent
Berg et al.

(10) Patent No.: US 7,908,089 B2
(45) Date of Patent: Mar. 15, 2011

(54) PATIENT CLASSIFICATION

(75) Inventors: Ellen L. Berg, Palo Alto, CA (US); Eugene C. Butcher, Portola Valley, CA (US); Jennifer Melrose, La Honda, CA (US)

(73) Assignee: BioSeek LLC, Burlingame, CA (US)

( * ) Notice: Subject to any disclaimer, the term of this patent is extended or adjusted under 35 U.S.C. 154(b) by 1449 days.

(21) Appl. No.: 10/856,564

(22) Filed: May 27, 2004

(65) Prior Publication Data

US 2004/0219592 A1    Nov. 4, 2004

Related U.S. Application Data

(60) Division of application No. 09/952,744, filed on Sep. 13, 2001, now Pat. No. 6,763,307, which is a continuation-in-part of application No. 09/800,605, filed on Mar. 6, 2001, now Pat. No. 6,656,695.

(60) Provisional application No. 60/186,976, filed on Mar. 6, 2000, provisional application No. 60/195,672, filed on Apr. 7, 2000.

(51) Int. Cl.
G06F 19/00 (2006.01)
G06F 17/30 (2006.01)
C12Q 1/00 (2006.01)

(52) U.S. Cl. ................. 702/19; 435/4; 707/3

(58) Field of Classification Search .......... None
See application file for complete search history.

(56) References Cited

U.S. PATENT DOCUMENTS

| 4,568,649 | A | 2/1986 | Bertoglio-Matte |
| 5,569,588 | A | 10/1996 | Ashby et al. |
| 5,631,153 | A | 5/1997 | Capecchi et al. |
| 5,777,888 | A | 7/1998 | Rine et al. |
| 5,994,076 | A | 11/1999 | Chenchik et al. |
| 6,004,755 | A | 12/1999 | Wang |
| 6,013,437 | A | 1/2000 | Luria et al. |
| 6,146,830 | A | 11/2000 | Friend et al. |
| 6,656,695 | B2 * | 12/2003 | Berg et al. .............. 435/7.21 |
| 6,763,307 | B2 * | 7/2004 | Berg et al. .............. 702/19 |
| 7,033,756 | B1 * | 4/2006 | Brinckerhoff et al. ...... 435/6 |

FOREIGN PATENT DOCUMENTS

| WO | WO 95/06132 | 3/1995 |
| WO | WO 96/23075 | 8/1996 |
| WO | 01/51664 | 7/2001 |
| WO | 02/44732 | 6/2002 |

OTHER PUBLICATIONS

Furukawa et al. Clinical Applications of the Histoculture Drug Response Assay. Clin. Cancer Res. vol. 1, pp. 305-311 (1995).*
Barton et al. Association Between Rheumatoid Arthritis and Polymorphism of Tumor Necrosis Factor Receptor II, But Not Tumor Necrosis Factor Receptor I, in Caucasians. Arthritis & Rheumatism vol. 44, pp. 61-65 (2001).*
Choy et al. Monoclonal Antibody Therapy in Rheumatoid Arthritis. British Journal of Rheumatology vol. 37, pp. 484-490 (1998).*
Iwakura et al. Pericardial Fluid from Patients With Unstable Angina Induces Vascular Endothelial Cell Apoptosis. Journal of the American College of Cardiology vol. 35, pp. 1785-1790 (2000).*
Tak et al. The Pathogenesis and Prevention of Joint Damage in Rheumatoid Arthritis. Arthritis and Rheumatism vol. 43, pp. 2619-2633 (2000).*
Fors et al. Large-scale SNP scoring from unamplified genomic DNA. Pharmacogenomics vol. 1, pp. 219-229 (2000).*
Monks et al. Tne NCI anti-cancer drug screen: a smart screen to identify effectors of novel targets. Anti-Cancer Drug Design vol. 12, pp. 533-541 (1997).*
Nickels et al. Detection of p53 in inflammatory tissue and lymphocytes using immunohistology and flow cytometry; a critical comment Journal of Clinical Pathology vol. 50, pp. 654-660 (1997).*
Partsch et al. T cell derived cytokines in psoriatic arthritis synovial fluids Annals of the Rheumatic Diseases vol. 57, pp. 691-693 (1998).*
Altschul et al. (Feb. 1994), "Issues in Searching Molecular Sequence Databases." *Nature Genetic*, vol. 6:119-129.
Blackstock et al. (Mar. 1999), "Proteomics: Quantitative and Physical Mapping of Cellular Proteins." *TIBTECH*, vol. 17:121-127.
Hatzimanikatis et al. (1999), "Proteomics: Theoretical and Experimental Considerations." *Biotechnol.*, vol. 15:312-318.
Mullner et al. (1998), "Proteomics: A New Way for Drug Target Discovery." *Arzneim-Forsch.*, vol. 48(1):93-95.
Nellen et al. (Nov. 1993), "What Makes an mRNA Anti-Sense-Itive?" *TIBS*, vol. 18:419-423.
May et al., Effects of Protein Tyrosine Kinase Inhibitors on Cytokine-Induced Adhesion Molecule Expression by Human Umbilical Vein Endothelial Cells, Brit. Journal, of Pharmacology, 1996, 118(7): 1761-1771.
Rice et al., Development of a Heigh Volume Screen to Identify Inhibitors of Endothelial Cell Activation, Analytical Biochem., 1996, 241(2): 254-259.
Hausner et al., The Comparative Growth Assay: Examining the Interplay of Anti-Cancer Agents With Cells Carrying Single Gene Alterations, Neoplasia, Doyma, 1999, 1(4): 356-367.
Heller et al., Discovery and Analysis of Inflammatory Disease-Related Genes Using CDNA Microarrays, Proc. Natl. Acad. Sci., (1997), 94: 2150-2155.
Bhalla et al., "Emergent properties of networks of biological signaling pathways," Science, 1999, 283(5400):381-387.
Hughes et al., "Functional discovery via a compendium of expression profiles," Cell, 2000, 102(1):109-126.
Lavé et al., "The use of human hepatocytes to select compounds based on their expected hepatic extraction ratios in humans," Pharm. Res., 1997, 14(2):152-155.
Schmidt-Weber, Carsten B; et al., "DNA Arrays in Allergy and Immunology", Int Arch Allergy Immunology, Sep. 1, 2001, 126(1):1-10.

* cited by examiner

*Primary Examiner* — John S Brusca
(74) *Attorney, Agent, or Firm* — Bozicevic, Field & Francis LLP; Pamela J. Sherwood

(57) ABSTRACT

Clinical patient tissue samples are classified according to the physiological status of cells present in the sample. In some embodiments of the invention, such cells are classified according to their ability to respond to therapeutic agents and treatments. In other embodiments, the cells or tissue samples are classified according to their status with respect to the activity of pathways of interest. The information thus derived is useful in prognosis and diagnosis, and can further be used develop surrogate markers for disease states, and to investigate the effect of genetic polymorphisms in the responsiveness and state of cells involved in disease.

11 Claims, 8 Drawing Sheets

- strong increase
- moderate increase
- unchanged
- moderate decrease
- strong decrease

PATIENT CLASSIFICATION

BACKGROUND OF THE INVENTION

In disease, as in health, there is a complex and changing cast of cells playing different roles. Functional capabilities of these cells can be altered, depending on the course of disease; as a result of underlying genetic differences; or due to drug exposure or other treatments. Even cancers, sometimes characterized as simple overgrowths of a single cell type, frequently show progression from one cell type to another. For example, in cancers of the breast and prostate there is a clear distinction between the steroid dependent and steroid independent cells, where the latter can emerge from the course of drug treatments. Similarly, the use of chemotherapeutics can select for resistant tumor cells, which are then able to persist through treatment. In other diseases, such as degenerative diseases, the loss of specific cell types is observed. For example, a key indicator of the severity of diabetes is the number of functioning islet cells that remain.

Apart from these diseased cells, normal cells in the body may be present, including the mobile cells of the immune system and angiogenic cells of the vascular system. Inflammatory diseases, as well as responses to infections, tumors and the like, are characterized by the presence of a variety of leukocytes, including B cells, T cells, polymorphonuclear cells (eosinophils, basophils and neutrophils), macrophages, natural killer cells, megakaryocytes, and the like. Even within one of these groups, there can be substantial variation in the function of the involved cells, for example a Th1 type T cells and a Th2 type T cells can have opposite effects on the course of a disease; and genetic and environmental effects can determine the onset and course of T cell-mediated diseases.

Angiogenesis is a process critical to both tumor growth and metastasis, and can be characterized by the presence of functionally distinct endothelial cells, which can vary in their responsiveness to cytokines and other growth and regulatory factors. Although angiogenesis is a continuous process, different consecutive steps can be identified, including release of pro-angiogenic factors and proteolytic enzymes, and endothelial cell migration, morphogenesis and proliferation. Under normal circumstances, the microvasculature is maintained in a quiescent state. The acquisition of the angiogenic phenotype depends on the outcome of stimulatory and inhibitory regulation by the tumur and its microenvironment, features which are modified by genetic differences.

In addition to the development and localization of cells, there is also genotypic variation, which can have important ramifications in an individuals response to therapy. Pharmacogenetics seeks to determine the linkage between an individual's genotype and that individual's ability to metabolize or react to a therapeutic agent. The use of pharmacogenetics is reviewed in *Annu Rev Pharmacol Toxicol* (2001); 41:101-121. Differences in metabolism or target sensitivity can lead to severe toxicity or therapeutic failure by altering the relation between bioactive dose and blood concentration of the drug. However, given the complex networks of interacting elements that confer an individuals responses to environmental or therapeutic or pathologic influences, simply predicting responses from genotype may be difficult. Thus, more direct means of assessing relevant patient phenotypes are required.

A need exists for methods that give detailed information about the "physiotype", embodying cellular events that occur in response to differences in cell's genetic makeup, changes in a cell, its environment, and other events that influence the biology of the host. The present invention satisfies this need and provides additional advantages.

Related Literature

Cell based assays include a variety of methods to measure metabolic activities of cells including: uptake of tagged molecules or metabolic precursors, receptor binding methods, incorporation of tritiated thymidine as a measure of cellular proliferation, uptake of protein or lipid biosynthesis precursors, the binding of radiolabeled or otherwise labeled ligands; assays to measure calcium flux, and a variety of techniques to measure the expression of specific genes or their gene products.

Compounds have also been screened for their ability to inhibit the expression of specific genes in gene reporter assays. For example, Ashby et al. U.S. Pat. No. 5,569,588; Rine and Ashby U.S. Pat. No. 5,777,888 describe a genome reporter matrix approach for comparing the effect of drugs on a panel of reporter genes to reveal effects of a compound on the transcription of a spectrum of genes in the genome.

Methods utilizing genetic sequence microarrays allow the detection of changes in expression patterns in response to stimulus. A few examples include U.S. Pat. No. 6,013,437; Luria et al., "Method for identifying translationally regulated genes"; U.S. Pat. No. 6,004,755, Wang, "Quantitative microarray hybridization assays"; and U.S. Pat. No. 5,994,076, Chenchik et al., "Methods of assaying differential expression". U.S. Pat. No. 6,146,830, Friend et al. "Method for determining the presence of a number of primary targets of a drug".

Proteomics techniques have potential for application to pharmaceutical drug screening. These methods require technically complex analysis and comparison of high resolution two-dimensional gels or other separation methods, often followed by mass spectrometry (for reviews see Hatzimanikatis et al. (1999) *Biotechnol Prog* 15(3):312-8; Blackstock et al. (1999) *Trends Biotechnol* 17(3):121-7. A discussion of the uses of proteomics in drug discovery may be found in Mullner et al. (1998) *Arzneimittelforschung* 48(1):93-5.

SUMMARY OF THE INVENTION

Methods and compositions are provided for the classification of clinical samples, e.g. patient tissue samples, according to the physiological status of cells or constituents present in the sample. The information thus derived is useful in prognosis and diagnosis, and can further be used develop surrogate markers for disease states, and to investigate the effect of genetic polymorphisms in the responsiveness and state of cells involved in disease. In some embodiments of the invention, such cells are classified according to their ability to respond to therapeutic agents and treatments. In other embodiments, the cells are classified according to their status with respect to the activity of pathways of interest. In another embodiment, patient tissue samples are evaluated for the presence of biologically active molecules, e.g. secreted factors and the like, by adding the patient sample to a cell culture responsive to the molecules.

Patient samples are cultured in a panel of environments, where each environment can comprise combinations of factors, cells and therapeutically active agents. Generally at least one environment contains multiple factors that affect pathways of interest. The effect of altering the culture environment is assessed by monitoring multiple output parameters. The cells may also be treated with therapeutic agents in the presence or absence of factors, and the profile of output parameters determined. A sufficient number of markers are selected to provide a high confidence level that the pathways of interest are being monitored. When factors are employed, a sufficient number of factors are used to involve one or a plurality of pathways and a sufficient number of markers are determined to insure the cellular status is accurately being monitored.

DETAILED DESCRIPTION OF THE EMBODIMENTS

Figure 1A:
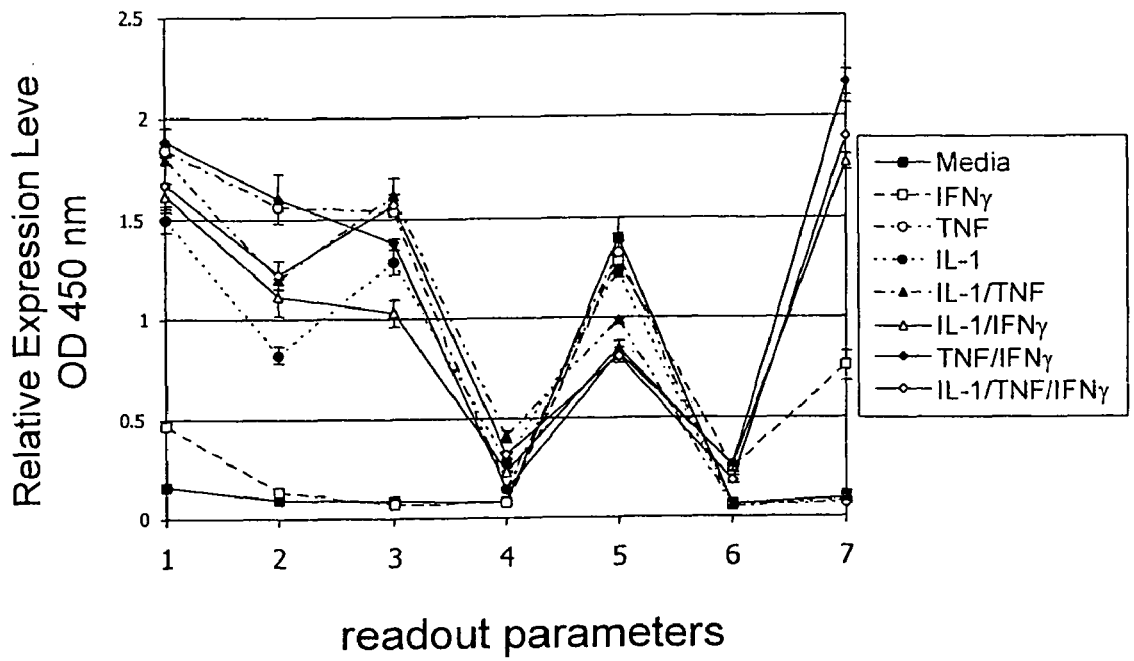
FIG. 1A-B. Assay combinations for charactering cells. A. Expression of selected readout parameters on selected assay combinations of HUVEC treated with proinflammatory cytokines. Confluent cultures of HUVEC cells were treated with TNFα (5 ng/ml), IFNγ (200 ng/ml) and or IL-1β (1 ng/ml). After 24 hours, cultures were washed and evaluated for the presence of the parameters ICAM-1 (1), VCAM-1 (2), E-selectin (3), IL-8 (4), CD31 (5), HLA-DR (6) and MIG (7) by cell-based ELISA. For this, plates were inverted until dry, blocked with 1% Blotto for 1 hr, and treated with primary antibodies (obtained from Pharmingen and Becton Dickinson) at 1 ng/ml for 1 hr. Plates were washed and secondary peroxidase-conjugated anti-mouse IgG antibody (Promega) at 1:2500 was applied for 1 hr. After washing, TMB substrate (Kierkegaard & Perry) was added and color developed. Development was stopped by addition of H2SO4 and the absorbance at 450 nm (subtracting the background absorbance at 650 nm) with a Molecular Devices plate reader. The relative expression levels of each parameter are indicated by the OD at 450 nm shown along the y-axis. The mean+/−SD from triplicate samples is shown. B. Visual representation of the data from FIG. 1A. The measurement obtained for each parameter is classified according to its relative change from the value obtained in the optimized assay combination (containing IL-1+TNF-α+IFN-γ), and represented by shaded squares. For each parameter and assay combination, the square is shaded by a checkerboard if the parameter measurement is unchanged (<20% above or below the measurement in the first assay combination (IL-1+TNF-α+IFNγ)) or p>0.05, n=3; slanted lines indicates that the parameter measurement is moderately increased (>20% but <50%); white indicates the parameter measurement is strongly increased (>50%); vertical lines indicates that the parameter measurement is moderated decreased (>20% but <50%); hatched lines indicates that the parameter measurement is strongly decreased (>50% less than the level measured in the first assay combination).

Methods and compositions are provided for the classification of clinical samples, e.g. patient tissue samples, cells, fluids, extracts of tissues, etc., according to the physiological status of cells present in the sample. The information thus derived is useful in prognosis and diagnosis, including susceptibility to disease(s), status of a diseased state and response to changes, in the environment, such as the passage of time, treatment with drugs or other modalities. The state of the cells provided in the clinical sample may be classified according to the activation of pathways of interest, for example T cells can be classified as Th1, Th2, or Th3 type cells. The cells can also be classified as to their ability to respond to therapeutic agents and treatments. Where the sample is being evaluated for the presence of biologically active molecules, the sample is added to a culture of potentially responsive cells, where the response of such cells is then monitored.

Based on changes in parameters in response to factors, information is derived that is useful in determining what pathways or cellular functionality is present in a tissue. Changes in parameters in response to therapeutic agents provides information that is informative of a patient's ability to respond to a drug in the context of a physiologically relevant microenvironment. Changes in parameters in response to therapeutic agents can be correlated with databases of BioMAPs for classification or to BioMAPs from control samples. In addition to classification, BioMAPs derived from clinical samples and therapeutic agents can be used to compare drugs that act on different pathways is a physiologically relevant environment.

The clinical samples can be further characterized by genetic analysis, proteomics, cell surface staining, or other means, in order to determine the presence of markers that are useful in classification. For example, genetic polymorphisms, such as single nucleotide polymorphisms or microsatellite repeats, can be causative of disease susceptibility or drug responsiveness, or can be linked to such phenotypes. Analysis of the genotype of a cell can be correlated to a BioMAP classification, and the information used in the development of genetic markers. Similarly, such marker as expression of cell surface proteins, presence of lipids, carbohydrates, etc. can be directly or indirectly associated with disease associated phenotypes, and with responsiveness to therapeutic agents and treatments.

The invention is also useful for screening compounds for drug interactions. Drug interactions can be problematic in cancer therapy. For example, while steroids control the edema that occurs with glioma, they also interfere with chemotherapy efficacy. Cytotoxic drugs form the basis of many cancer therapies, thus interference with chemotherapy efficacy may offset any anti-tumor effects of angiogenesis inhibitors. Most cytotoxic drugs effect both normal and neoplastic cells, although at different concentrations, therefore, screening compounds in the presence of cytotoxic drugs can be performed and reveal unexpected interference or beneficial synergies. Interactions between a cytotoxic drug and any test compound is detected by the observation of BioMAPs obtained in the presence of both drugs that are inconsistent with additive effects.

Patient samples are cultured in a panel of environments, where each environment can comprise combinations of factors, cells and therapeutically active agents. Generally at least one environment contains multiple factors that affect pathways of interest. The effect of altering the culture environment is assessed by monitoring multiple output parameters. The cells may also be treated with therapeutic agents in the presence or absence of factors, and the profile of output parameters determined. A sufficient number of markers are selected to provide a high confidence level that the pathways of interest are being monitored. When factors are employed, a sufficient number of factors are used to involve one or a plurality of pathways and a sufficient number of markers are determined to insure the cellular status is accurately being monitored.

For convenience, a clinical sample comprising cells may be referred to as "test cells", and will comprise one or more types of cells present in a clinical sample. For example, a tissue sample may include endothelial cells, a variety of lymphocytes and other hematopoietic cells, tumor cells which may be clonal or polyclonal in origin, and the like. The test cells need not be directly involved in a disease of interest.

A clinical sample may also be evaluated for the presence of biologically active factors and other molecules, where such non-cellular material is indicative of the physiological state of the tissue from which it is obtained. Such samples are evaluated for their effect on one or a panel of cells, as described in co-pending patent application Ser. No. 09/800,605.

The term "assay combinations" refers to such cultures, where test cells are contacted with medium and multiple combination of factors, agents and other culture variations. These cell cultures are created by the addition of a sufficient number of different factors to provoke a response that simulates cellular physiology of a state of interest, and to allow for the status of cells in culture to be determined in relation to a change in an environment. The state of interest will normally involve a plurality of pathways where the pathways regulate a plurality of parameters or markers identifying a phenotype associated with the state of interest. In a preferred embodiment, one or more assay combinations are provided that simulate physiological cell states of interest, particularly physiological cell states in vivo, usually using the same type of cells or combinations, of cells. Such a simulation will usually include at least three different regulated features (parameters) shared with in vivo cell counterparts in normal or diseased states. Alternatively, the simulation will include a cell culture system that allows discrimination of modifications in at least three different signaling pathways or cell functions operative in vivo under conditions of interest.

A phenotype of the test cells that is useful for monitoring output parameters can be generated by including a plurality of factors, and optionally additional cells, e.g. stromal cells, endothelial cells, fibroblasts, etc., that may interact with the patient tissue. The factors and cells inducing pathways induce a response in the test cells in vitro. Such factors are naturally occurring compounds, e.g. known compounds that have surface membrane receptors and induce a cellular signal that results in a modified phenotype; or synthetic compounds that mimic such naturally occurring factors. In some instances, factors will act intracellularly by passing through the cell surface membrane and entering the cytosol with binding to components in the cytosol, nucleus or other organelle. In referring to factors, it is understood that it is the activities of the factors that are of interest and not necessarily a particular naturally occurring factor itself.

For each test cell there are a number of markers that can be measured, which relate to specific pathways associated with the cell type and condition. As described in co-pending U.S. patent application Ser. No. 09/800,605, which disclosure is specifically incorporated by reference, at least about 4 markers are identified that allow for evaluating the up or down regulation of at least 2 pathways, generally three or more pathways, where the total number of markers will usually not exceed 8. The markers are selected to provide a robust picture of the status of the cell, due to its condition, e.g. pro-inflammatory, immunosuppressive, neoplastic, etc., its response to therapy, its response to a drug, or the like. Each set of markers will define a set of cell pathways and their response. However, there will normally be at least 2, usually at least 3, common markers for the particular determination.

The nature and number of parameters measured generally reflects the response of a plurality of pathways. The subject approach provides for robust results having enhanced predictability in relation to the status of the test cells. The results may be compared to the basal condition, tissue matched normal controls, and/or the condition in the presence of one or more of the factors, particularly in comparison to all of the factors used in the presence and absence of agent. The effects of different environments are conveniently provided in BioMAPs, where the results can be mathematically compared.

BioMAP

A BioMAP is prepared from values obtained by measuring parameters or markers of the test cells in the presence and absence of different factors, and/or by comparing the presence of an agent of interest and at least one other state, usually the control state, which may include the state without agent or with a different agent. Parameters include cellular products or epitopes thereof, as well as functional states, whose levels vary in the presence of the factors. Desirably, the results are normalized against a standard, usually a "control value or state," to provide a normalized data set. Values obtained from test conditions can be normalized by subtracting the unstimulated control values from the test values, and dividing the corrected test value by the corrected stimulated control value. Other methods of normalization can also be used; and the logarithm or other derivative of measured values or ratio of test to stimulated or other control values may be used. Data is normalized to control data on a cell type under control conditions, but a BioMAP may comprise normalized data from one, two or multiple cell types and assay conditions.

By referring to a BioMAP is intended that the dataset will comprise values of the levels of at least two sets of parameters obtained under different assay combinations. Depending on the use of the BioMAP, the BioMAP may also include the parameter values for each the factors included in the assay combination, individually and/or together with fewer than the entire assay combination. The parameter values are usually created electronically and stored in a data processor for comparison with other BioMAPs and databases compiled from the BioMAPs.

A graph of a BioMAP can be presented visually as numerical values, symbols, color gradations, or the like, indicating the parameter values. The graph is conveniently presented where color and/or design provide an indication of the level of the particular marker. The indicators may be vertical or horizontal as to the individual markers and the assay combinations, so that by looking at the graph, one can immediately compare the levels of the different markers for each of the combinations and discern patterns related to the assay combinations and the differences between assay combinations. In this way, one can rapidly relate different candidate pharmacologic agents, the pathways they affect and their efficacy in modulating the individual pathways.

Optionally, a BioMAP can be annotated to indicate information about the sources of information for the dataset. Annotations may include, for example, the number of assay conditions in a panel (n); controls used for normalization (N); parameters (P), which may be designated for the number and identity of the parameters; environmental changes, such as the addition of factors and/or agents or a change in the physical conditions (V); cell type (C); and the like. The annotation may further specify specific factors or conditions present in one of the assay combinations, e.g. n1, n2, n3, etc., where the presence of factors in the assay combination is designated (F), temperature may be designated (T), pH, etc. The parameters may also be designated in this as, e.g. P1=ICAM-1, P2=VCAM-1, P3=E-selectin, etc. Written out, the annotation may be set forth as: (v) B {n; N; P; C; F}.

A database of BioMAPs can be compiled from sets of experiments, for example, a database can contain BioMAPs obtained from clinical samples such as sites of inflammation, tumors, etc., each in a panel of assay combinations, with multiple different environmental changes, where each change can be a series of related compounds, or compounds representing different classes of molecules. In another embodiment, a database comprises BioMAPs from one compound, with multiple different cell panels.

Mathematical systems can be used to compare BioMAPs, and to provide quantitative measures of similarities and differences between them. For example, the BioMAPs in the database can be analyzed by pattern recognition algorithms or clustering methods (e.g. hierarchical or k-means clustering, etc.) that use statistical analysis (correlation coefficients, etc.) to quantify relatedness of BioMAPs. These methods can be modified (by weighting, employing classification strategies, etc.) to optimize the ability of a BioMAP to discriminate different functional effects. For example, individual parameters can be given more or less weight when analyzing the dataset of the BioMAP, in order to enhance the discriminatory ability of the BioMAP. The effect of altering the weights assigned each parameter is assessed, and an iterative process is used to optimize pathway or cellular function discrimination.

In many cases the literature has sufficient information to establish assay combinations to provide a useful BioMAP. Where the information is not available, by using the procedures described in the literature for identifying markers for diseases, microarrays for RNA transcription comparisons, proteomic or immunologic comparisons, between normal cells and cells in the disease state, one can ascertain the endogenous factors associated with the disease state and the markers that are produced by the cells associated with the disease state.

Biomap analysis can be used to optimize cell culture conditions. Additional markers can be deduced and added as a marker to the map. The greater the number of individual markers that vary independently of each other, the more robust the BioMAP. If desired, the parameters of the BioMAP can be optimized by obtaining BioMAP parameters within an assay combination or panel of assay combinations using different sets of readout, and using pattern recognition algorithms and statistical analyses to compare and contrast different BioMAPs of different parameter sets. Parameters are selected that provide a BioMAP that discriminates between changes in the environment of the cell culture known to have different modes of action, i.e. the BioMAP is similar for agents with a common mode of action, and different for agents with a different mode of action. The optimization process allows the identification and selection of a minimal set of parameters, each of which provides a robust readout, and that together provide a BioMAP that enables discrimination of different modes of action of stimuli or agents. The iterative process focuses on optimizing the assay combinations and readout parameters to maximize efficiency and the number of signaling pathways and/or functionally different cell states produced in the assay configurations that can be identified and distinguished, while at the same time minimizing the number of parameters or assay combinations required for such discrimination.

Clinical Samples

Clinical samples for use in the methods of the invention may be obtained from a variety of sources, including blood, lymph, cerebrospinal fluid, synovial fluid, tissue biopsies, skin, saliva, lavage, and the like. Such samples can comprise complex populations of cells, which can be assayed as a population, or separated into sub-populations, and can also comprise acellular samples. Such cellular and acellular sample can be separated by centrifugation, elutriation, density gradient separation, apheresis, affinity selection, panning, FACS, centrifugation with Hypaque, etc. By using antibodies specific for markers identified with particular cell types, a relatively homogeneous population of cells may be obtained. Alternatively, a heterogeneous cell population can be used. Acellular samples can be separated according to immunologic or biochemical criteria, for example by various electrophoretic and chromatographic means, as is known in the art.

Once a sample is obtained, it can be used directly, frozen, or maintained in appropriate culture medium for sport periods of time. Various media can be employed to maintain cells during the classification process. There are established protocols for the culture of diverse cell types that reflect their in vivo counterparts. Protocols may require the use of special conditions and selective media to enable cell growth or expression of specialized cellular functions.

Such methods are described in the following: Animal Cell Culture Techniques (Springer Lab Manual), Clynes (Editor), Springer Verlag, 1998; Animal Cell Culture Methods (Methods in Cell Biology, Vol 57, Barnes and Mather, Eds, Academic Press, 1998; Harrison and Rae, General Techniques of Cell Culture (Handbooks in Practical Animal Cell Biology), Cambridge University Press, 1997; Endothelial Cell Culture (Handbooks in Practical Animal Cell Biology), Bicknell (Editor), Cambridge University Press, 1996; Human Cell Culture, Cancer Cell Lines Part 1: Human Cell Culture, Masters and Palsson, eds., Kluwer Academic Publishers, 1998; Human Cell Culture Volume II—Cancer Cell Lines Part 2 (Human Cell Culture Volume 2), Masters and Palsson, eds., Kluwer Academic Publishers, 1999; Wilson, Methods in Cell Biology: Animal Cell Culture Methods (Vol 57), Academic Press, 1998; Current Protocols in Immunology, Coligan et al., eds, John Wiley & Sons, New York, N.Y., 2000; Current Protocols in Cell Biology, Bonifacino et al., eds, John Wiley & Sons, New York, N.Y., 2000.

The methods of the invention find use in a wide variety of animal species, including mammalian species. Animal models, particularly small mammals, e.g. murine, lagomorpha, etc. are of interest for experimental investigations. Humans are of particular interest for both diagnostic and prognostic applications of the method.

The samples may come from any organ or compartment of the body, to the extent the cells can be obtained by any convenient procedure, such as the drawing of blood, venipuncture, biopsy, or the like. Cell types that can find use in the subject invention, include endothelial cells, muscle cells, myocardial, smooth and skeletal muscle cells, mesenchymal cells, epithelial cells; hematopoietic cells, such, as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells; etc.; adipocytes, cells involved with particular organs, such as thymus, endocrine glands, pancreas, brain, such as neurons, glia, astrocytes, dendrocytes, etc. and in some instances, may even involve genetically modified cells thereof. Hematopoietic cells will be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc. Usually a sample will comprise at least about $10^2$ cells, more usually at least about $10^3$ cells, and preferable $10^4$ or more cells.

Assay Combinations

The term "environment," or "culture condition", as used in the assay combinations of the subject methods encompasses cells, media, factors, time and temperature. Environments may also include drugs and other compounds, particular atmospheric conditions, pH, salt composition, minerals, etc. The conditions will be controlled and the BioMAP will reflect the similarities and differences between each of the assay combinations involving a different environment or culture condition.

Culture of cells is typically performed in a sterile environment, for example, at 37° C. in an incubator containing a humidified 92-95% air/5-8% $CO_2$ atmosphere. Cell culture may be carried but in nutrient mixtures containing undefined biological fluids such as fetal calf serum, or media which is fully defined and serum free.

Culture protocols may require the use of special conditions and selective media to enable cell growth or expression of specialized cellular functions. Such methods are described in the following: Animal Cell Culture Techniques (Springer Lab Manual), Clynes (Editor), Springer Verlag, 1998; Animal Cell Culture Methods (Methods in Cell Biology, Vol 57, Barnes and Mather, Eds, Academic Press, 1998; Harrison and Rae, General Techniques of Cell Culture (Handbooks in Practical Animal Cell Biology), Cambridge University Press, 1997; Endothelial Cell Culture (Handbooks in Practical Animal Cell Biology), Bicknell (Editor), Cambridge University Press, 1996; Human Cell Culture, Cancer Cell Lines Part 1: Human Cell Culture, Masters and Palsson, eds., Kluwer Academic Publishers, 1998; Human Cell Culture Volume II—Cancer Cell Lines Part 2 (Human Cell Culture Volume 2), Masters and Palsson, eds., Kluwer Academic Publishers, 1999; Wilson, Methods in Cell Biology: Animal Cell Culture Methods (Vol 57), Academic Press, 1998; Current Protocols in Immunology, Coligan et al., eds, John Wiley & Sons, New York, N.Y., 2000; Current Protocols in Cell Biology, Bonifacino et al., eds, John Wiley & Sons, New York, N.Y., 2000.

Some preferred environments include environments that discriminate or emphasize cell or tissue states associated with pathology in one or more diseases, for example, Th1 versus Th2 polarization of effector T cells; prothrombotic; inflammatory (e.g. NFκB, upregulated TNF-α cytokine production, downregulated IL-10, TGFβ, etc.; dysregulated proliferation (neoplasia); angiogenesis; etc.) Environments that facilitate discrimination of specific signaling pathways implicated in disease states are also of interest, e.g. NFκB, classic Th1 or Th2 induction environments, etc.

A assay combinations are used in classifying and investigating complex states of cells, frequently resulting from cellular interactions, which may frequently involve at least about two, frequently three, or more different cell types and/or will involve a plurality of soluble factors that are present in a physiological fluid, particularly as the result of a physiological event, e.g. infection, neoplasia, autoimmune, etc. that is, frequently involving more than one cell type and more than one factor. The measured parameters may be obtained from one or more of the cell types. The cells in the assay combination, either one or up to each of the different cell types, can have identifying characteristics allowing them to be distinguished during analysis. Various techniques may be employed to identify the cells in the assay combination for analysis of the parameters of interest.

Conditions of interest include inflammatory processes that occur in response to infection, trauma, etc., autoimmune diseases, such as diabetes, lupus, arthritis, etc., cardiovascular diseases, such as stroke, atherosclerosis, etc., neoplasia, hyperplasia, addiction, infection, obesity, cellular degeneration, apoptosis, senescence, differentiation, and the like.

Multifactorial, usually involving multicellular, assay combinations, may reflect many of the conditions indicated above, such as inflammatory processes; autoimmune diseases; cardiovascular diseases; tumors, etc. That is, a multiplicity of factors are employed to influence a plurality of cellular pathways and a multiplicity of parameters are measured that reflect the status of the pathways. Degenerative diseases, including affected tissues and surrounding areas, may be exploited to determine both the response of the affected tissue, and the interactions with other cell types or other parts of the body.

Factors added to the cultures can be the products of other cell types, for example, expressed proteins associated with a disease, can be compounds that simulate naturally occurring factors, can be surface membrane proteins free of the membrane or as part of microsomes, or other reagent that induces the appropriate pathway to aid in the simulation of the phenotype or provides the appropriate environment to simulate the physiological condition. Factors (including mimetics thereof) can be added individually or in combination, from feeder cells, may be added as a bolus or continuously, where the factor is degraded by the culture, etc.

Illustrative naturally occurring factors include cytokines, chemokines, and other factors, e.g. growth factors, such factors include GM-CSF, G-CSF, M-CSF, TGF, FGF, EGF, TNF-α, GH, corticotropin, melanotropin, ACTH, etc., extracellular matrix components, surface membrane proteins, such as integrins and adhesins, and other components that are expressed by the targeted cells or their surrounding milieu in vivo, etc., that may be isolated from natural sources or produced by recombinant technology or synthesis, compounds that mimic the action of other compounds or cell types, e.g. an antibody which acts like a factor or mimics a factor, such as synthetic drugs that act as ligands for target receptors. For example, in the case of the T cell receptor, the action of an oligopeptide processed from an antigen and presented by an antigen-presenting cell, etc. can be employed. Where a family of related factors are referred to with a single designation, e.g. IL-1, VEGF, IFN, etc., in referring to the single description, any one or some or all of the members of the group are intended, where the literature will be aware of how the factors are to be used in the context of the assay combination. Components may also include soluble, or immobilized recombinant or purified receptors, or antibodies against receptors or ligand mimetics.

Cancer cells may be cultured with different factors based on the different cells in the environment of the tumor, as well as other factors in the blood induced by factors secreted by the neoplastic cells. Many of these factors will be the same factors described above, but additional factors include factors associated with angiogenesis, such as angiogenin, angiopoietin-1, HGF, PDGF, TNF-α, VEGF, IL-1, IL-4, IL-6, IL-8 and fibronectin.

Panels

For the most part, the BioMAP dataset will comprise data from a panel of assay combinations. The panel will be related to the purpose of the BioMAP and may include not only the information that has been developed substantially concurrently with the study, but also information that has been previously developed under comparable conditions. Frequently a panel will be used that is comprised of at least one assay combination that provides for simulation of multiple pathways of interest, while other assay combinations in the panel are variants thereof. The number of combinations in a panel may vary with the particular use. For example, the minimum number of assay combinations will be two for a panel for initial screening that would comprise a single assay combination. A panel for characterizing the mechanism of action of an active compound will usually comprise a plurality of assay combinations, usually at least about 4, more usually at least 6, frequently at least about 10 and may be as many as 20 or more unique combinations.

In another embodiment, the panel comprises culture conditions where multiple specific changes are made to the culture environment, e.g. two or more changes, usually not more than about 6, more usually not more than about 4. Such changes are associated with the additional information that is engendered by the indicated variations. The variations can include the addition of known inhibitors of specific pathways.

Parameters

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assay combinations, usually at least about 2 of the same assay combination will be performed to provide a value. Variability is expected and a range of values for each of the set of test parameters will be obtained using standard statistical methods with a common statistical method used to provide single values.

Markers are selected to serve as parameters based on the following criteria, where any parameter need not have all of the criteria: the parameter is modulated in the physiological condition that one is simulating with the assay combination; the parameter is modulated by a factor that is available and known to modulate the parameter in vitro analogous to the manner it is modulated in vivo; the parameter has a robust response that can be easily detected and differentiated and is not too sensitive to concentration variation, that is, it will not substantially differ in its response to an over two-fold change; the parameter is secreted or is a surface membrane protein or other readily measurable component; the parameter desirably requires not more than two factors to be produced; the parameter is not co-regulated with another parameter, so as to be redundant in the information provided; and in some instances, changes in the parameter are indicative of toxicity leading to cell death. The set of parameters selected is sufficiently large to allow distinction between reference patterns, while sufficiently selective to fulfill computational requirements.

For each assay combination, certain parameters will be functionally relevant and will be altered in response to test or reference agents or conditions, while other parameters may remain static in that particular combination. Biomaps will generally comprise only functionally relevant parameter information, although a static parameter may serve as an internal control. A typical BioMAP will comprise data from at least 3 functionally relevant parameters, more usually at least about 5 functionally, relevant parameters, and may include 10 or more functionally relevant parameters, usually not more than about 30, more usually not more than about 20, parameters. In analyzing the data from the BioMAP, all of the parameters need not be weighed equally. Those parameters that are closely functionally associated with the disease state or pathophysiologic response, and/or with modulation of cell pathways of interest may be given greater weight in evaluating a candidate drug or a readout, as compared to other parameters that are suggestive, but do not have as strong an association.

Parameters of interest include detection of cytoplasmic, cell surface or secreted biomolecules, frequently biopolymers, e.g. polypeptides, polysaccharides, polynucleotides, lipids, etc. Cell surface and secreted molecules are a preferred parameter type as these mediate cell communication and cell effector responses and can be more readily assayed. In one embodiment, parameters include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric integrins. A parameter may be detection of a specifically modified protein or oligosaccharide, e.g. a phosphorylated protein, such as a STAT transcriptional protein; or sulfated oligosaccharide, or such as the carbohydrate structure Sialyl Lewis x, a selectin ligand. The presence of the active conformation of a receptor may comprise one parameter while an inactive conformation of a receptor may comprise another, e.g. the active and inactive forms of heterodimeric integrin $\forall_m\exists_2$ or Mac-1.

A parameter may be defined by a specific monoclonal antibody or a ligand or receptor binding determinant. Parameters may include the presence of cell surface molecules such as CD antigens (CD1-CD247), cell adhesion molecules including $\alpha_4\beta_7$ and other integrins, selectin ligands, such as CLA and Sialyl Lewis x, and extracellular matrix components. Parameters may also include the presence of secreted products such as lymphokines, including IL-2, IL-4, IL-6, growth factors, etc. (Leukocyte Typing VI, T. Kishimoto et al., eds., Garland Publishing, London, England, 1997); Chemokines in Disease: Biology and Clinical Research (Contemporary Immunology), Hebert, Ed., Humana Press, 1999.

For activated T cells these parameters may include IL-1R, IL-2R, IL4R, IL-12Rβ, CD45RO, CD49E, tissue selective adhesion molecules, homing receptors, chemokine receptors, CD26, CD27, CD30 and other activation antigens. Additional parameters that are modulated during activation include MHC class II; functional activation of integrins due to clustering and/or conformational changes; T cell proliferation and cytokine production, including chemokine production. Of particular importance is the regulation of patterns of cytokine production, the best-characterized example being the production of IL-4 by Th2 cells, and interferon-γ by Th1 T cells. The ability to shift cytokine production patterns in vivo is a powerful means of modulating pathologic immune responses, for example in models of EAE, diabetes, inflammatory bowel disease, etc. Thus, the expression of secreted cytokines may be a preferred class of parameters, detectable, for example, by ELISA analysis of the supernatants, etc.

Therapeutic Agents

In many cases, it will be of interest to determine whether a patient is responsive to a particular therapeutic agent or regimen. In particular, it is of interest to determine the efficacy of such therapies in a biologically relevant context, i.e. in the presence of factors and interacting cells. Included are pharmacologically active drugs, genetically active molecules, etc. Compounds of interest include chemotherapeutic agents, anti-inflammatory agents, hormones or hormone antagonists, ion channel modifiers, and neuroactive agents. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference.

Classification Methods

Cells and samples are classified by adding a therapeutic agent or treatment; and/or by culturing cells in combinations of factors, in at least one and usually a plurality of assay combinations to form a panel of assay combinations, usually in conjunction with positive and negative controls. The change in parameter readout in response to an agent, sample or factors is measured, desirably normalized, and the resulting BioMAP may then be evaluated by comparison to reference BioMAPs. The reference BioMAPs may include basal readouts in the presence and absence of the factors, BioMAPs obtained with other agents, which may or may not include known inhibitors of known pathways, etc. Agents of interest for analysis include any biologically active molecule with the capability of modulating, directly or indirectly, the phenotype of interest of a cell of interest.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol*. 17(12):477-81). Thus, antibodies can be genetically modified to provide a fluorescent dye as part of their structure The use of high affinity antibody binding and/or structural linkage during labeling provides dramatically reduced non-specific backgrounds, leading to clean signals that are easily detected. Such extremely high levels of specificity enable the simultaneous use of several different fluorescent labels, where each preferably emits at a unique color. Fluorescence technologies have matured to the point where an abundance of useful dyes are now commercially available. These are available from many sources, including Sigma Chemical Company (St. Louis Mo.) and Molecular Probes (Handbook of Fluorescent Probes and Research Chemicals, Seventh Edition, Molecular Probes, Eugene Oreg.). Other fluorescent sensors have been designed to report on biological activities or environmental changes, e.g. pH, calcium concentration, electrical potential, proximity to other probes, etc. Methods of interest include calcium flux, nucleotide incorporation, quantitative PAGE (proteomics), etc.

Highly luminescent semiconductor quantum dots (zinc sulfide-capped cadmium selenide) have been covalently coupled to biomolecules for use in ultrasensitive biological detection (Stupp et al. (1997) *Science* 277(5330):1242-8; Chan et al. (1998) *Science* 281(5385):2016-8). Compared with conventional fluorophores, quantum dot nanocrystals have a narrow, tunable, symmetric emission spectrum and are photochemically stable (Bonadeo et al. (1998) *Science* 282 (5393):1473-6). The advantage of quantum dots is the potential for exponentially large numbers of independent readouts from a single source or sample.

Multiple fluorescent labels can be used on the same sample and individually detected quantitatively, permitting measurement of multiple cellular responses simultaneously. Many quantitative techniques have been developed to harness the unique properties of fluorescence including: direct fluorescence measurements, fluorescence resonance energy transfer (FRET), fluorescence polarization or anisotropy (FP), time resolved fluorescence (TRF), fluorescence lifetime measurements (FLM), fluorescence correlation spectroscopy (FCS), and fluorescence photobleaching recovery (FPR) (Handbook of Fluorescent Probes and Research Chemicals, Seventh Edition, Molecular Probes, Eugene Oreg.).

Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules or cytokines, or the average fluorescence intensity, the median fluorescence intensity, the variance in fluorescence intensity, or some relationship among these.

As an example, Luminex beads or other fluorescent beads, or beads varying in light scattering parameters can be conjugated to antibodies to cytokines or other parameters, or conjugated to protein receptors for parameters. The conjugated beads are added to the cells, cell lysate, or to the removed supernatant, allowing bead binding to target parameters. Also, fluorescent antibody to a distinct epitope of the target parameter is used to measure the level of target parameter bound. The fluorescence and light scatter characteristics of the beads constitute an identified of the target parameter, and fluorescence derived from added antibody to the target parameter is an indication of the quantity of target parameter bound, and hence a readout of the individual parameter.

Flow cytometry may be used to quantitate parameters such as the presence of cell surface proteins or conformational or posttranslational modification thereof; intracellular or secreted protein, where permeabilization allows antibody (or probe) access, and the like. Brefeldin A is commonly utilized to prevent secretion of intracellular substances. Flow cytometry methods are known in the art, and described in the following: Flow Cytometry and Cell Storing (Springer Lab Manual), Radbruch, Ed., Springer Verlag, 2000; Ormerod, Flow Cytometry, Springer Verlag, 1999; Flow Cytometry Protocols (Methods in Molecular Biology, No 91), Jaroszeski and Heller, Eds., Humana Press, 1998; Current Protocols in Cytometry, Robinson et al., eds, John Wiley & Sons, New York, N.Y., 2000. The readouts of selected parameters are capable of being real simultaneously, or in sequence during a single analysis, as for example through the use of fluorescent antibodies to cell surface molecules. As an example, these can be tagged with different fluorochromes, fluorescent bead tags, e.g. quantum dots, etc., allowing analysis of up to 4 or more fluorescent colors simultaneously by flow cytometry. Plug-flow flow cytometry that has the potential to automate the delivery of small samples from unpressurized sources at rates compatible with many screening and assay applications, may allow higher throughput, compatible with high throughput screening, Edwards et al. (1999) *Cytometry* 37:156-9.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3):313-24, for examples.

Identifiers of individual cells, for example different cell types or cell type variants, may be fluorescent, as for example labeling of different unit cell types with different levels of a fluorescent compound, and the like. If two cell types are to be mixed, one may be labeled and the other not. If three or more are to be included, each may be labeled to different levels of fluorescence by incubation with different concentrations of a labeling compound, or for different times. As identifiers, of large numbers of cells, a matrix of fluorescence labeling intensities of two or more different fluorescent colors may be used, such that the number of distinct unit cell types that are identified is a number of fluorescent levels of one color, e.g., carboxyfluorescein succinimidyl ester (CFSE), times the number of fluorescence levels employed of the second color, e.g. tetramethylrhodamine isothiocyanate (TRITC), or the like, times the number of levels of a third color, etc. Alternatively, intrinsic light scattering properties of the different cell types, or characteristics of the BioMAPs of the test parameters included in the analysis, can be used in addition to or in place of fluorescent labels as unit cell type identifiers.

Data Analysis

The comparison of a BioMAP obtained from test cells, and a reference BioMAP(s) is accomplished by the use, of suitable deduction protocols, AI systems, statistical comparisons, etc. Preferably, the BioMAP is compared with a database of reference BioMAPs. Similarity to reference BioMAPs from normal cells, cells from similarly diseased tissue, from cell lines with responses induced by assay combinations involving known pathway stimuli or inhibitors, and the like, can provide an initial indication of the cellular pathways activated in the test cells, and the responsiveness of the test cells to a therapeutic regimen.

A database of reference BioMAPs can be compiled. These databases may include reference BioMAPs from panels that include known agents or combinations of agents that target specific pathways, as well as references from the analysis of cells treated under environmental conditions in which single or multiple environmental conditions or parameters are removed or specifically altered. Reference BioMAPs may also be generated from panels containing cells with genetic constructs that selectively target or modulate specific cellular pathways. In this way, a database is developed that can reveal the contributions of individual pathways to a complex response.

The effectiveness of pattern search algorithms in classifying BioMAPs can involve the optimization of the number of parameters and assay combinations. The disclosed techniques for selection of parameters provide for computational requirements resulting in physiologically relevant outputs. Moreover, these techniques for pre-filtering data sets (or potential data sets) using cell activity and disease-relevant biological information improve the likelihood that the outputs returned from database searches will be relevant to predicting agent mechanisms and in vivo agent effects.

For the development of an expert system for selection and classification of biologically active drug compounds or other interventions, the following procedures are employed. For every reference and test pattern, typically a data matrix is generated, where each point of the data matrix corresponds to a readout from a parameter, where data for each parameter may come from replicate determinations, e.g. multiple individual cells of the same type. As previously described, a data point may be quantitative, semi-quantitative, or qualitative, depending on the nature of the parameter.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

Classification rules are constructed from sets of training data (i.e. data matrices) obtained from multiple repeated experiments. Classification rules are selected as correctly identifying repeated reference patterns and successfully distinguishing distinct reference patterns. Classification rule-learning algorithms may include decision tree methods, statistical methods, naive Bayesian algorithms, and the like.

A knowledge database will be of sufficient complexity to permit novel test BioMAPs to be effectively identified and classified. Several approaches for generating a sufficiently encompassing set of classification patterns, and sufficiently powerful mathematical/statistical methods for discriminating between them can accomplish this.

A database can be compiled by preparing BioMAPs using different combinations of a plurality of biologically active factors, in conjunction with BioMAPs involving the use of known agents having known effects and/or the use of genetically modified cells, where the genetic modification affects one or more of the pathways affected by one or more of the factors used to create the phenotype. For example, if the culture conditions selected to produce a specific in vitro reference pattern contain four biologically active agents, in addition to those present in the basal conditions of the normal or basal environment, a BioMAP would be generated from a panel of cells treated under all possible combinations of the 4 agents (15 assay conditions), typically using constant concentrations in each of the combinations. The extent of the database associated with assay combinations to screen candidates for specific phenotypes, e.g. indications, will vary with the nature of the phenotype, the amount of information desired, the complexity of the system, and the like.

The data from cells treated with specific drugs known to interact with particular targets or pathways provide a more detailed set of classification readouts. Data generated from cells that are genetically modified using over-expression techniques and anti-sense techniques, permit testing the influence of individual genes on the phenotype.

As indicated, agents may be analyzed in the absence of any factors or with a limited number of factors. The assay is performed as previously described and the values of the parameters can be compared to the BioMAP reflecting the values for the parameters of the physiologic state of interest, the values of the parameters for the response to one or more factors, and the basal response. In this way, the effect of the agent under physiological conditions can be evaluated. Similarly, one may have datasets compiled from combinations of agents to determine their effect when combined on cell physiology.

A preferred knowledge database contains reference BioMAPs comprising data from optimized panels of cells, environments and parameters. For complex environments, data reflecting small variations in the environment may also be included in the knowledge database, e.g. environments where one or more factors or cell types of interest are excluded or included or quantitatively altered in, for example, concentration or time of exposure, etc.

Disease Markers

Cells from a clinical sample that are suspected of having a marker that is associated with or causative of disease can be analyzed for the presence of genetic polymorphisms or other markers. Genetic characterization analyzes DNA or RNA, from any source, e.g. skin, cheek scrapings, blood samples, etc. The nucleic acids are screened for the presence of a polymorphism of interest, e.g. SNPs, microsatellite markers, and the like.

A number of methods are available for analyzing nucleic acids for the presence or absence of a specific sequence. Where large amounts of DNA are available, genomic DNA is used directly. Analysis of genomic DNA may use whole chromosomes or fractionated DNA, e.g. Southern blots, etc. Comparative Genomic Hybridization (CGH), as described in U.S. Pat. No. 5,665,549, provides methods for determining the relative number of copies of a genomic sequence. The intensity of the signals from each labeled subject nucleic acid and/or the differences in the ratios between different signals from the labeled subject nucleic acid sequences are compared to determine the relative copy numbers of the nucleic acid sequences as a function of position along the reference chromosome spread. Other methods for fluorescence in situ hybridization are known in the art, for a review, see Fox et al. (1995) *Clin Chem* 41(11):1554-1559.

Alternatively, the region of interest is cloned into a suitable vector and grown in sufficient quantity for analysis. Cells that express genes of interest may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of techniques may be found in Sambrook, et al. *Molecular Cloning: A Laboratory Manual*, CSH Press 1989, pp. 14.2☐14.33. Alternatively, various methods are known in the art that utilize oligonucleotide ligation as a means of detecting polymorphisms, for examples see Riley et al. (1990) *N.A.R.* 18:2887-2890; and Delahunty et al. (1996) *Am. J. Hum. Genet.* 58:1239-1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$p, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. genomic DNA, amplification product or cloned fragment, is analyzed by one of a number of methods known in the art. The nucleic acid may be sequenced by dideoxy or other methods, and the sequence of bases compared to the sequence of genes of interest. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility.

Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Changes in the promoter or enhancer sequence that may affect expression levels of genes of interest can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

Microsatellite linkage analysis may be performed alone, or in combination with direct detection of polymorphisms. The use of microsatellite markers for genotyping is well documented. For examples, see Mansfield et al. (1994) Genomics 24:225-233; Ziegle et al. (1992) Genomics 14:1026-1031; Dib et al., supra. Microsatellite loci have non-repetitive flanking sequences that uniquely identify the particular locus, and a central repeat motif that is at least 2 nucleotides in length, up to 7, usually 2-4 nucleotides in length. Repeats can be simple or complex. The number of repeats at a specific locus are polymorphic in a population, thereby generating individual differences in the length of DNA that lies between the repeats. The number will vary from at least 1 repeat to as many as about 100 repeats or more. Primers can be used to amplify the region of genomic DNA that contains the repeats. Conveniently, a detectable label will be included in the amplification reaction. Multiplex amplification may be performed in which several sets of primers are combined in the same reaction tube. This is particularly advantageous when limited amounts of sample DNA are available for analysis. Conveniently, each of the sets of primers is labeled with a different fluorochrome. After amplification, the products are size fractionated. Fractionation may be performed by gel electrophoresis, particularly denaturing acrylamide or agarose gels. A convenient system uses denaturing polyacrylamide gels in combination with an automated DNA sequencer, see Hunkapillar et al. (1991) Science 254:59-74. The automated sequencer is particularly useful with multiplex amplification or pooled products of separate PCR reactions. Capillary electrophoresis may also be used for fractionation. A review of capillary electrophoresis may be found in Landers, et al. (1993) BioTechniques 14:98-111. The size of the amplification product is proportional to the number of repeats that are present at the locus specified by the primers. The size will be polymorphic in the population, and is therefore an allelic marker for that locus.

Screening for markers, e.g. surrogate markers for a disease condition, may be based on the functional or antigenic characteristics of the protein. Various immunoassays may be used in screening. Functional protein assays are also effective screening tools, for example by detecting the specific phosphatase, kinase, protease, or other enzymatic activity in a sample. Alternatively, changes in electrophoretic mobility may be used.

Antibodies may be used in staining or in immunoassays. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a fluorescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc. An alternative method for diagnosis depends on the in vitro detection of binding between antibodies proteins in a lysate. A conventional sandwich type assay may be used. Other immunoassays are also known in the art and may find use as diagnostics. Ouchterlony plates provide a simple determination of antibody binding. Western blots may be performed on protein gels or protein spots on filters, using a detection system specific for PC-1 as desired, conveniently using a labeling method as described for the sandwich assay.

Endothelial Cells

The present invention is useful for classification of endothelial cells according to their physiologic state. Endothelial cells are found in inflammatory tissues; they are highly responsive to environmental stimuli; and they are a cell type for which primary cells can be readily isolated and cultured. For example, vascular endothelial cells participate in the inflammatory disease process by regulating the type of leukocytes that are recruited to the target tissue. The specificity of recruitment is determined by the combinatorial expression of adhesion molecules and chemokines. A number of factors are known to be associated with endothelial cells, such as EGF, FGF, VEGF, insulin, etc., cytokines, such as the interleukins, including IL-1 IL-3, IL-4, IL-8 and IL-13; interferons, including IFN-α, IFN-β, IFN-γ; chemokines; TNF-α, TGFβ, proangiogenic and anti-angiogenic factors, etc. (See Current Protocols in Immunology, supra.).

Endothelial cells in inflammatory tissues from chronic inflammatory disease patients differ from endothelial cells in normal tissues by increased expression parameters including ICAM-1, E-selectin, IL-8 and HLA-DR [Nakamura S, Lab Invest 1993, 69:77-85; Geboes K, Gastroenterology 1992, 103:439-47; Mazzucchelli L, J Pathol 1996, 178:201-6]. In addition, each of these parameters has been demonstrated to function in the inflammatory disease process. ICAM-1 and E-selectin are cell adhesion molecules that contribute to the localization and activity of inflammatory cells including T cells, monocytes, and neutrophils. IL-8 is a neutrophil chemoattractant and HLA-DR participates in the activity of pathologic T cells. Other cell surface or secreted parameters include parameters that are known to be regulated by factors, such as VCAM-1, which is induced on endothelial cells by TNF-α or IFN-γ; IL-10 and MIG which are induced on endothelial cells by IFN-γ; or GRO-α or ENA-78 which are induced on endothelial cells by IL-1 and/or TNF-α [Goebeler M, J Invest Dermatol 1997, 108:445-51; Piali L Eur J Immunol. 1998, 28:961-72].

The highly responsive nature of endothelial cells makes them particularly useful in co-culture, such as with patient samples, as their response due to factors from the patient sample or due to interactions with patient samples can give specific information regarding the state of the patient sample.

Leukocytes

Lymphokine-producing activated lymphocytes (CD45RO+, CD44hi, etc.) are a hallmark of inflammatory diseases including psoriasis, rheumatoid arthritis, Crohn's disease, ulcerative colitis, asthma, etc. Depending on the disease environment and tissue site, activated lymphocytes can differ in their expression and function of adhesion molecules and other receptors, as well as in their production of various cytokines and other factors. The ability to selectively block lymphocyte activation associated with the inflammatory disease without inhibiting or suppressing lymphocyte activation associated with the ability to fight infection and neoplasia is a goal of inflammatory drug therapy.

Specific homing and adhesion receptors, as well as chemokine receptors, expressed by lymphocytes differentiating into effector and memory cells target the involved regulatory and cytotoxic T cell populations, as well as B cells responsible for humoral immunity. Upregulation and modulation of homing receptor expression patterns is observed when lymphocytes are activated in defined microenvironments comprising specific cytokines; and in some environments multiple homing receptors (e.g., $\alpha_4\beta_7$, the cutaneous lymphocyte antigen ("CLA"), inflammatory chemokine receptor such as CCR5 and CXCR3 and bonzo, etc.) are induced. Multiplex analysis of each of these homing receptor parameters, which may also be performed in conjunction with other parameters in reflecting the cellular state of activation, can be used to select immunomodulatory compounds capable of shifting patterns of homing receptor expression in a common microenvironment. Such modulators of lymphocyte targeting can be powerful immunosuppressives for localized immune pathologies, as in inflammatory bowel diseases, psoriasis, multiple sclerosis, arthritis, and the like; modulating patterns of lymphocyte homing/targeting molecules they would modulate in vivo immune responses therapeutically without the side effects associated with generalized immunosuppression.

The assay conditions for these cells include (1) known activation conditions ((combinations of anti-CD3+IL-2+/− IL-4+/−IFN-γ+/−IL-12+/−anti-IL-4 or anti-IFN-γ). Such conditions are given in: T Cell Protocols: Development and Activation (Methods in Molecular Biology, 134), Kearse, Ed., Humana Press, 2000). Assay combinations and reference BioMAPs are identified for a variety of diseases, including psoriasis, arthritis, Crohn's disease, ulcerative colitis, asthma, etc.

The disease environment in psoriasis includes IL-12, IFN-γ and TNF-γ (Yawalker, 1998, J. Invest. Dermatol. 111:1053; Austin, 1999, J. Invest. Dermatol. 113:752), therefore an assay combination for psoriasis will include one or more, usually at least two, and frequently all of these factors. Inflammatory T cells in psoriasis express high levels of the CLA antigen, a carbohydrate antigen related to Sialyl Lewis x (Berg, 1991, J. Exp. Med. 174:1461; Picker, 1990, Am. J. Pathol. 136:1053). Therefore a parameter set for psoriasis will contain the CLA antigen.

The disease environment in Crohn's disease includes IL-1, TNF-α, IL-6, IL-8, IL-12, IL-18, and IFN-γ (Daig, 1996; Woywodt, 1994; Kakazu, 1999; Pizarro, 1999; Monteleone, 1999), therefore an assay combination for Crohn's disease will include one or more of these factors, generally including at least two of the IL factors, by themselves or in combination with at least one of IFN-γ and TNF-α. T cells in inflammatory bowel disease express high levels of the αEβ7 integrin (Elewaut, 1998, Scand J. Gastroenterol, 33:743), therefore the parameter set for inflammatory bowel diseases preferentially contains αEβ7

The disease environment in rheumatoid arthritis includes TNF-α, IL-1, IL-6, IL-10, IL-15, MIP1 β MCP-1, and TGF β (Robinson, 1995, Clin. Exp. Immunol. 101:398; Thurkow, 1997, J. Pathol. 181:444; Suzuki, 1999, Int. Immunol, 11:553), therefore an assay combination for arthritis-will include one or more of these factors, generally including at least two of the IL factors and at least one of MIP1 and MCP-1. T cells in rheumatoid arthritis synovial fluid express CCR5 and CXCR3 (Suzuki, 1999; Qin, 1998, J. Clin. Invest. 101:746; Loetscher, 1998, Nature 391:344), therefore the parameter set for rheumatoid arthritis preferentially contains CCR5 and CXCR3.

The disease environment in asthma includes IL-1β, IL-4, IL-5, IL-6 and GM-CSF (Miadonna, 1997; Walker, 1994), therefore, an assay combination for asthma will contain one or more of these factors, generally including at least two of the IL factors and GM-CSF.

Macrophage

Peripheral blood monocytes, tissue macrophages and related cells can be screened pharmacologically active compounds/interventions. Monocytes/macrophages in different physiological settings have altered responses. IL-4 reduces production of IL-10 in LPS stimulated blood monocytes but not in synovial monocyte/macrophages (Bonder (1999) Immunol. 96:529; Ju (1999) *Int. Rev. Immunol.* 18:485). In addition to being highly responsive to their environment, monocytes/macrophages participate in a variety of disease processes, including inflammation, fibrosis, and wound healing, through their production of mediators, growth factors, phagocytosis and antigen presentation functions. Assay combinations, e.g. IL-4 and other IL factors, M-CSF, and GM-CSF are used in combination with each other or other factors associated with the physiologic or disease environments of interest and readout parameter sets are selected that allow different states to be distinguished. Readout parameters include integrins, adhesion molecules, and the like.

Mast Cell

The present invention can be applied to the classification of mast cell activation, and the responsiveness of mast cells to therapeutic agents, e.g. in the treatment of allergy and asthma, where mast cell products mediate disease pathology (Galli, 2000, Curr. Opin. Hematol. 7:32). Mast cells display altered responses depending on their environment. The ability of mast cells to produce IL-3 and GM-CSF is significantly increased in the presence of fibronectin or vitronectin (Kruger-Krasagakes, 1999, Immunology, 98:253). Mast cells in allergen-induced late-phase cutaneous reactions in atopic patients express high levels of the high affinity IgE receptor compared with mast cells in control skin (Ying, 1998, Immunology 93:281). Assay combinations including at least one of fibronectin and vitronectin are developed that reflect physiologic or disease environments and readout parameter sets, including at least one of IL-3, GM-CSF, and IgE-receptor, are selected that allow different states to be distinguished. Reference patterns, held in a knowledge database include those developed from the analysis of cells treated under environmental conditions in which single components are removed, or with known drugs that target specific pathways.

Cancer Applications

The invention is also useful for classification of cancer cells and other associated cells present in tumors, e.g. endothelial cells, lymphocytes, etc., and for testing agents that have therapeutic activity. Drug interactions are highly important in cancer therapy. For example, while steroids control the edema that occurs with glioma, they also interfere with chemotherapy efficacy. Cytotoxic drugs are a main treatment for cancer and interference with the chemotherapy efficacy may offset the anti-tumor effect of an apoptosis inducer. On the other hand, synergy between individual drugs would be highly beneficial, perhaps allowing reduced doses of the individual drugs and reducing the side effects.

The present invention can be applied to the classification of the metastatic phenotypes of cancer cells. Metastatic cancers have altered adhesive and invasive functions. Metastatic cancers are associated with certain features including expression of various oncogenes, such as H-ras, increased levels of proteolytic enzymes, such as TPA (tissue plasminogen activator), production of osteopontin, and altered adhesion molecule expression and function. For example, carcinomas preferentially express α6 β1 and less α2β1, α3β1, and α5β1 (Chambers 1993, Crit. Rev. Oncol. 4:95; Dedhar, 1995, Cancer Metastasis Rev. 14:165; Tuck, 1999, Oncogene 18:4237). Simultaneous multiplex analyses of normal and cancer cell lines allows discrimination of agents that selectively modulate the metastatic phenotype.

There is a general inverse relationship between the degree of cellular differentiation and the rate of cell proliferation in tumors. Several anti-cancer agents stimulate the differentiation and inhibit proliferation of malignant cells, including retinoids, various cytokines and analogs of vitamin D (Bollag, 1994, J. Cell Biochem. 56:427). All-trans retinoic acid, an agent that induces differentiation, gives a high rate of complete clinical remission in the treatment of acute promyelocytic leukemia (Tallman, 1994, Semin Hematol 31 (Suppl 5):38). Agents that stimulate differentiation are not easily detected using traditional in vitro assays of anticancer drug activity.

The present invention can be applied determine the effectiveness compounds that induce apoptosis of tumor endothelial cells. Tumor endothelium differs from other endothelium by increased expression of αvβ3. A set of conditions that induce apoptosis of these cells is evaluated and a set of parameters that defines a BioMAP diagnostic of apoptosis is identified. Apoptotic conditions are identified as those that induce DNA laddering, and other well described features. These include simple culture conditions that contain one or more factors known to induce or promote endothelial cell apoptosis in vitro, such as ceremide, the combination of TNF-α and heat shock or sodium arsenite, TNF-α+IFN-γ, oxysterols; TNF-α in the presence of cyclohexamine, etc. (See Ruegg (1998) Nat. Med. 4:408). Parameters that may be included in the selected set include a variety of molecules involved in adhesion and proteolysis (since a prominent feature of apoptotic endothelial cells is their release from the vessel wall), those that can be modulated by individual factors, such as E-selectin, ICAM-1, VCAM and HLA-DR, and molecules or determinants known to be modulated with apoptosis such as CD95, ICAM-1, CD44, and carbohydrate determinants (Herbst, 1999, J. Cell Physiol. 181:295; Rapaport, 1999, Glycobiology 9:1337; Hirano (1999) Blood 93:2999; Thomas (1998) J. Immunol. 161:2195; Ma (1998) Eur. J. Hematol. 61:27; Pober (1998) Pathol. Biol. (Paris) 46:159).

Angiogenesis Inhibitors

The present invention can be applied to the classification of cells with respect to potential for angiogenesis. Pharmacologic modulation of angiogenesis has applications to the treatment of cancer, where vascularization of tumors contributes to cancer growth; for inflammatory conditions such as arthritis where neovascularization supports inflammatory cell influx; wound healing; and others. A number of biologically active agents are known to induce or promote angiogenesis including VEGF, FGF, IL-8, IL-4, various extracellular matrix components, etc., where at least 2, usually at least 3 of these factors may be used in an assay combination. Vascularizing arthritis environments contain basic FGF and VEGF in addition to TNF-α, IL-1, IL-6, IL-10, IL-15, MIP1β and MCP-1 (Qu, 1995, Lab Invest., 73:339; Koch, J. Immunol. 1994, 152:4149; Robinson, 1995, Clin. Exp. Immunol. 101: 398; Thurkow, 1997, J. Pathol. 181:444; Suzuki, 1999, Int. Immunol, 11:553). The disease environments of highly vascularized tumors includes hypoxia, VEGF, fibrinogen and TGF-β (Senger, 1994 Invasion Metastasis, 95:385; Shweiki, 1992, Nature, 359:843). Parameters include adhesion molecules, receptors, chemokines, etc., that are known to be differentially expressed by angiogenic endothelium at the disease sites. These may include the expression of functional forms of adhesion molecules such as αvβ3, VCAM, proteases, such as matrix metalloproteinases, or other substances.

Kits. For convenience, the systems of the subject invention may be provided in kits. The kits would include the appropriate additives for providing the simulation, reagents for measuring the parameters, software for preparing the BioMAP, and comparison BioMAPs with patient information and outcome. The factors will be selected that in conjunction with the cells would provide the desired physiological state simulating the in vivo situation. The factors could be a mixture in the appropriate proportions or provided individually. For example, IL-1, TNF-α, and IFN-γ would be combined as a powder to be measured for addition to the cell medium and labeled antibodies to parameters, such as ICAM-1, VCAM-1 and E-selectin, in conjunction with second capture antibodies or using antibodies for homogeneous assays, where another reagent is present. The software will receive the results and create a BioMAP and will include data from other determinations of analogous situations for comparison. The software can also normalize the results with the results from a basal culture and/or the basal culture including the factors.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Example 1

Regulators of Endothelial Cell Responses to Inflammation

The present invention is useful for identifying regulators of inflammation using human endothelial cells as an indicator cell type. A set of assay combinations that reproduces aspects of the response of the endothelial cells to different types of inflammatory processes is developed in vitro.

Primary human umbilical vein endothelial cells (HUVEC) are used. Other cells that may replace HUVEC in the screen include primary microvascular endothelial cells, aortic or arteriolar endothelial cells or endothelial cell lines such as EAhy926 or E6-E7 4-5-2G cells or human telomerase reverse transcriptase-expressing endothelial cells (Simmons, J. Immunol., 148:267, 1992; Rhim, Carcinogenesis 19:673, 1998; Yang, J. Biol. Chem. 274:26141, 1999). $2 \times 10^4$ cells/ml are cultured to confluence in EGM-2 (Clonetics). Other media that may replace EGM-2 include EGM (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984). The disease environment present in chronic inflammatory diseases, such as Crohn's disease, differs from the normal condition by increased presence of multiple biologically active agents including IL-1β, TNF-α, and IFN-γ (Woywodt, 1994; Kakazu, 1999). Other biologically active agents that may be increased in chronic inflammatory disease environments include IL-4, IL-6, IL-8, IL-12, IL-13, IL-18, TGFbeta, and histamine, as well as activated leukocytes and their products (Daig, 1996, Gut 38:216; Woywodt, 1994, Eur. cytokine Netw. 5:387; Kakazu 1999 Am J. Gastroenterol. 94:2149; Pizarro, 1999, J. Immunol. 162:6829; Monteleone, 1999, J. Immunol. 163:143; McClane, 1999 J Parenter Enteral Nutr 23:S20; Beck, 1999, Inflam. Bowel Dis. 5:44). Optimized assay combinations will contain at least two, and preferably three, four or more of these biologically active agents. Concentrations of agents are standard according to the literature, typically at physiologic concentrations. Concentrations may also be determined experimentally as the amount required to saturate the relevant receptor. A useful feature of the present invention is that combinatorial effects of multiple factors are observed over wide ranges of factor concentrations. Based on the factors included in an assay combination, a set of parameters for including in a BioMAP are selected.

Selection of parameters is based on the following factors: 1) parameters that are modulated in vivo in the disease environment or condition; 2) parameters that are modulated by one of the components in the assay combination; 3) parameters that are modulated by more than one of the components in the assay combination; 4) parameters that are modulated by the combined action of two or more components in the assay combination; 5) parameters that participate in the disease process, such as validated disease targets; 6) cell surface and secreted molecules. Preferred parameters are functional and are downstream within signaling pathways, so as to provide information on effects of multiple pathways. For assay combinations containing the factors TNFα, IFN-γ and IL-1, parameters examined and chosen by these criteria include ICAM-1 (CD54), VCAM-1 (CD106), E-selectin (CD62E), IL-8, HLA-DR and MIG (CLCX9). Other parameters of interest for including in a Biomap include: IP-10, Eotaxin-1, Eotaxin-3, MCP-1, RANTES, Tarc, CD31, alphavbeta3, and P-selectin (CD62P). Parameters examined but not selected include: CD34, CD40, CD9, CXCR2, CD95, fibronectin, HLA-ABC, GROalpha, MCP-4, TAPA-1, alphaVbeta5, VE-Cadherin, CD44, von Willebrand factor, CD141, 142, 143, and CD151. Parameters are not selected for inclusion in a BioMAP for the following reasons: redundancy, function of parameter is not associated with disease pathology, function is upstream in a signaling pathway, parameter is not modulated in response to factors, modulation is not robust or reproducible. Cell death in inflammation, involved for example in cellular remodelling in healing, as well as the consequences of toxicity, involves apoptosis. Parameters of interest also include parameters indicative of cell damage and apoptosis including released cytoplasmic lactate dehydrogenase (LDH) or mitochondrial cytochrome c, appearance of APO2.7 epitope or active caspase-3 (Zhang, J. Immunol., 157:3980, 1996; Bussing, Cytometry 37:133, 1999). Parameters indicative of cell proliferation are also of interest and include Ki-67 and PCNA (Landberg Cytometry, 13:230, 1992).

Figure 1B:
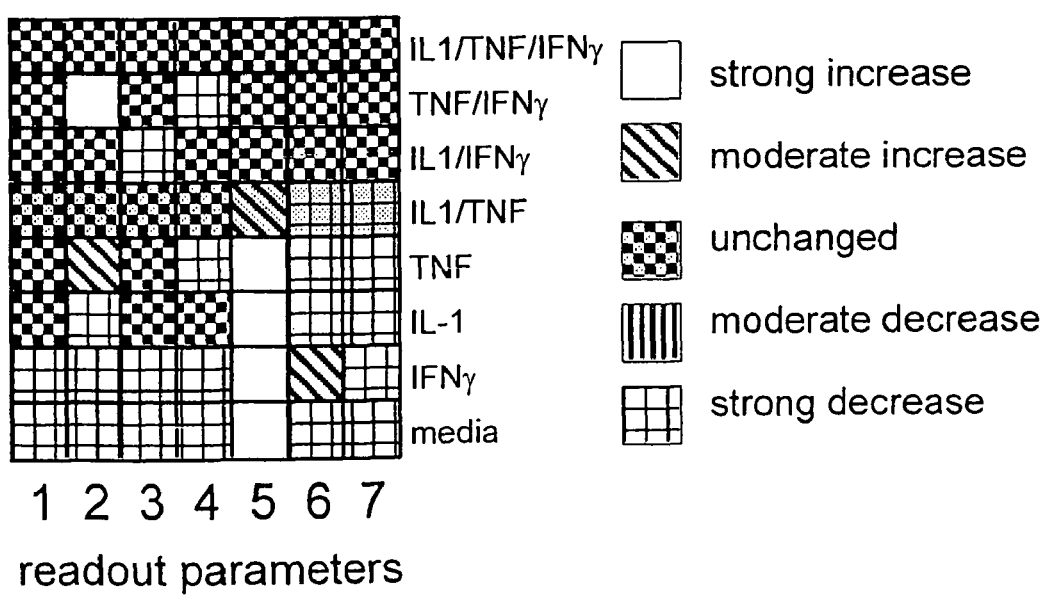

The experiments shown in FIG. 1A-1B illustrate the usefulness of the present invention in compound screening applications. FIG. 1A shows the readout patterns from confluent cultures of HUVEC incubated with either of IFN-γ (100 ng/ml), TNF-α (5 ng/ml), IL-1 (1 ng/ml), two or more of these in combination, or basal medium for 24 hours. After 24 hours, cultures are washed and evaluated for the presence of the parameters ICAM-1 (1), VCAM-1 (2), E-selectin (3), IL-8 (4), CD31 (5), HLA-DR (6) and MIG (7) by cell-based ELISA as described (Melrose, J. Immunol. 161:2457, 1998). For this, plates are blocked with 1% Blotto for 1 hr, and treated with primary antibodies (obtained from Pharmingen and Becton Dickinson) at 1 ng/ml for 2 hr. After washing, secondary peroxidase-conjugated anti-mouse IgG antibody (Promega) at 1:2500 is applied for 45 min. After washing, TMB substrate (Kierkegaard & Perry) is added and color developed. Development is stopped by addition of $H_2SO_4$ and the absorbance at 450 nm (subtracting the background absorbance at 600 nm) is read with a Molecular Dynamics plate reader. The relative expression levels of each parameter are indicated by the OD at 450 nm shown along the y-axis. The mean+/−SD from triplicate samples is shown.

FIG. 1B shows a visual representation of the data from FIG. 1A, where the measurement obtained for each parameter is classified according to its relative change from the value obtained in the optimized assay combination (containing IL-1+TNF-α+INF-γ), and represented by shaded squares. For each parameter and assay combination, the square is shaded by a checkerboard if the parameter measurement is unchanged (<20% above or below the measurement in the first assay combination (IL-1+TNF-α+INF-γ)) or p>0.05, n=3; slanted lines indicates that the parameter measurement is moderately increased (>20% but <50%); white indicates the parameter measurement is strongly increased (>50%); vertical lines indicates that the parameter measurement is moderated decreased (>20% but <50%); hatched lines indicates that the parameter measurement is strongly decreased (>50% less than the level measured in the first assay combination).

As shown in FIG. 1A, HUVEC cultured with IFN-γ for 24 hours express increased levels of ICAM-1, HLA-DR and MIG, compared to cells cultured with media alone, as measured by cell-based ELISA. HUVEC cultured with TNF-α for 24 hours express increased levels of cell surface ICAM-1, VCAM-1, and E-selectin. HUVEC cultured in the presence of both TNF-α and IFN-γ for 24 hours produce a combined phenotype where HUVEC express increased levels of ICAM-1, VCAM-1, E-selectin, HLA-DR and MIG. This phenotype is more similar to the in vivo phenotype of endothelial cells in chronic inflammation and moreover reflects the stimulation (and interaction) of two different known pathways of interest in regulation of inflammatory processes. Addition of IL-1 to the assay combination containing TNF-α and IFN-γ further alters the phenotype resulting in increased levels of E-selectin and IL-8 (shown in FIG. 1A), in addition to the increased levels of ICAM-1, VCAM-1, HLA-DR and MIG. E-selectin and IL-8 are particularly correlated with disease stage in chronic inflammatory diseases, including inflammatory bowel disease (MacDermott, 1999, J. Clin. Immunol. 19:266; Koizumi, 1992, Gastroenterology 1992103:840). Concentrations of IL-1β, TNF-α and IFN-γ employed and length of exposure are standard according to the literature. Concentrations and exposure length are also tested experimentally and conditions chosen to achieve an endothelial cell phenotype displaying multiple features of endothelial cells in chronic inflammatory diseases (e.g increased expression of ICAM-1, VCAM-1, E-selectin as well as HLA-DR and MIG). However, a particularly useful feature of the invention is that the combined phenotype is observed over a wide range of concentrations of the individual biologically active factors. Thus an assay combination containing IL-1, TNF-α and IFN-γ represents an optimized assay combination. This assay combination is useful for screening for compounds that modulate aspects of IL-1, TNF-α or IFN-γ signaling pathways. In particular, it provides a useful screen for selecting compounds that are active when a particular target pathway may be modified by the activity of other pathways or when the target is not known.

In subsequent panels one or more of IL-4, IL-6, IL-8, IL-12, IL-13, IL-18, TGFbeta, and histamine are applied; and/or neutralizing antibodies to autocrine factors such as IL-6, IL-1 and IL-8. Standard concentrations of agents are employed as described in the literature. Based on the factors selected, a set of parameters for including in a BioMAP is selected.

Database of readout response patterns. A database of reference BioMAPs is compiled for the optimized assay combination and parameter set of the example described in FIG. 1. These reference BioMAPs are developed from assay combinations in which specific modifications of the optimized assay combination are made. These modifications included: 1) elimination of one or more assay combination components, 2) addition of compounds or interventions to the assay combination. Biological responses, particularly responses in primary human cells can display significant variability from day to day and from donor to donor. One important aspect of the present invention is that while absolute amounts of parameters can vary substantially between assays, combinatorial responses provide for less variability and the process of normalization to produce a BioMAP provides cellular activity profiles that are robust and reproducible.

Figure 2A:
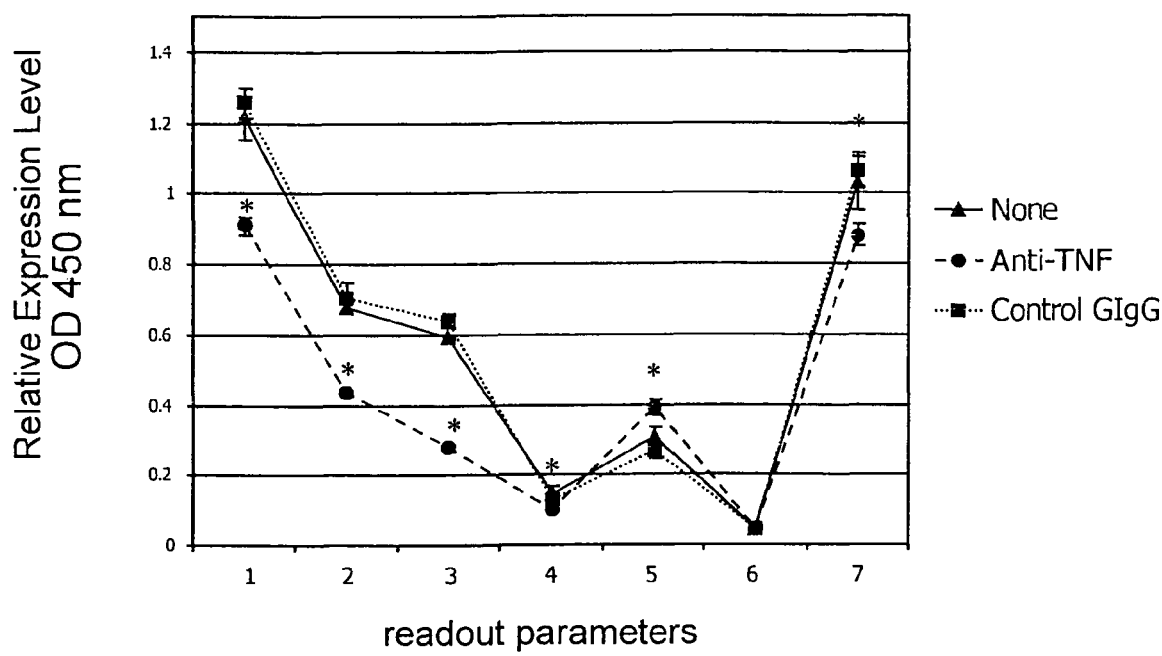
FIG. 2A-B. Assay combinations for characterizing cells. Confluent cultures of HUVEC cells were treated with TNFα (5 ng/ml), IFNγ (200 ng/ml) and IL-1β (1 ng/ml) in the presence or absence of neutralizing anti-TNFα (R&D Systems) or control Goat anti-IgG. After 24 hours, cultures were washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. A. The relative expression of each parameter is shown along the y-axis as average value of the OD measured at 450 nm of triplicate samples. The mean+/−SD from triplicate samples are shown. * indicates p<0.05 comparing results obtained with anti-TNFα to the control. B. Visual representation of the data from FIG. 2A. The measurement obtained for each parameter is classified according to its relative change from the value obtained in the optimized assay combination (containing IL-1+TNF-α+IFN-γ), and represented by shaded squares. For each parameter and assay combination, the square is shaded by a checkerboard if the parameter measurement is unchanged (<20% above or below the measurement in the first assay combination (IL-1+TNF-α+IFN-γ)) or p>0.05, n=3; slanted lines indicates that the parameter measurement is moderately increased (>20% but <50%); white indicates the parameter measurement is strongly increased (>50%); vertical lines indicates that the parameter measurement is moderated decreased (>20% but <50%); hatched lines indicates that the parameter measurement is strongly decreased (>50% less than the level measured in the first assay-combination).
Figure 2B:
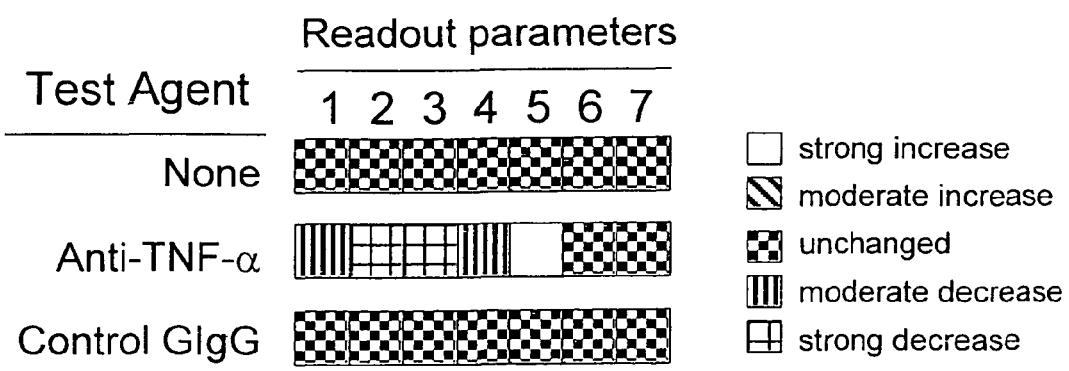

An inhibitor of TNF-α is an active compound in the optimized assay combination described above. Addition of neutralizing anti-TNF-α antibodies to this assay combination results in reduced expression levels of ICAM-1, VCAM-1, E-selectin, IL-8, and MIG, and increased expression levels of CD31 (FIG. 2A). Confluent cultures of HUVEC cells are treated with TNF-α (5 ng/ml)+IFNγ (100 ng/ml)+IL-1 (1 ng/ml) in the presence or absence of neutralizing anti-TNF-α or control antibody (Goat anti-IgG). After 24 hours, cultures are washed and evaluated for the cell surface expression of ICAM-1 (1), VCAM-1 (2), E-selectin (3), IL-8 (4), CD31(5), HLA-DR (6) and MIG (7) by cell-based ELISA performed as described in FIG. 1. In FIG. 2A, the relative expression of each parameter is shown along the y-axis as average value of the OD measured at 450 nm of triplicate samples. The mean+/−SD from triplicate samples are, shown. * indicates p<0.05 comparing results obtained with anti-TNF-α to the control.

Figure 3A:
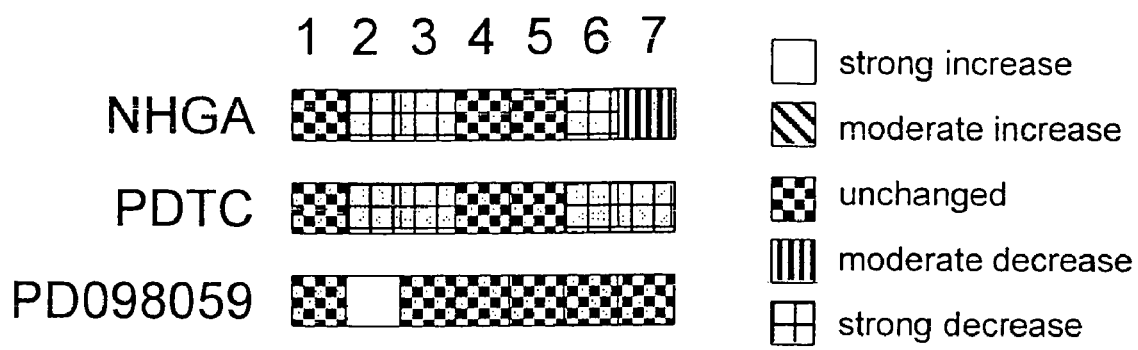
FIG. 3A-C. Effect of NFκB inhibitors NHGA and PDTC, MAP kinase inhibitor PD098059, or ibuprofen on the expression of readout parameters in the inflammatory BioMAP assay combination containing three factors (IL-1+TNF-α+IFN-γ). Confluent cultures of HUVEC cells were treated with TNFα (5 ng/ml), IFNγ (200 ng/ml) and IL-1β (1 ng/ml) in the presence or absence of (A) 10 µM NHGA, 200 µM PDTC or 9 µM PD098059; (B) 125-500 µM ibuprofen. Compounds were tested at the highest concentration at which they were soluble, and/or did not result in loss of cells from the plate. After 24 hours, cultures were washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. The measurement obtained for each parameter is classified according to its relative change from the value obtained in the optimized assay combination (containing IL-1+TNF-α+INF-γ), and represented by shaded squares. For each parameter and assay combination, the square is shaded by a checkerboard if the parameter measurement is unchanged (<20% above or below the measurement in the first assay combination (IL-1+TNF-α+INF-γ)) or p>0.05, n=3; slanted lines indicates that the parameter measurement is moderately increased (>20% but <50%); white indicates the parameter measurement is strongly increased (>50%); vertical lines indicates that the parameter measurement is moderated decreased (>20% but <50%); hatched lines indicates that the parameter measurement is strongly decreased (>50% less than the level measured in the assay combination without compounds). C. Effect of compounds on the reference readout pattern in the inflammatory BioMAP assay combination containing three factors (IL-1+TNF-α+INF-γ). Confluent cultures of HUVEC cells were treated with TNFα (5 ng/ml), IFNγ (200 ng/ml) and IL-1β (1 ng/ml) in the presence or absence of compounds as listed in Table I. After 24 hours, cultures were washed and evaluated for the cell surface expression of parameters of ICAM-1, VCAM-1, E-selectin, IL-8, CD31, HLA-DR and MIG by cell-based ELISA performed as described in FIG. 1. The resulting BioMAPs were compared and correlation coefficients employed in clustering analysis (Clustal X program). Readout patterns are as visualized by a tree diagram in which a) each terminal branch point represents the readout pattern from one assay combination in one experiment; b) the length of the vertical distance from the upper horizontal line (no change and control patterns) to the termini are related to the extent of difference in the readout pattern from the control pattern (without drug); and c) the distance along the branches from one terminal pattern value to another reflects the extent of difference between them. Similar patterns are thus clustered together. The figure illustrates the reproducibility of patterns resulting from treatment with a single drug in multiple experiments, and those resulting from multiple drugs that target the same signaling pathway.
Figure 3B:
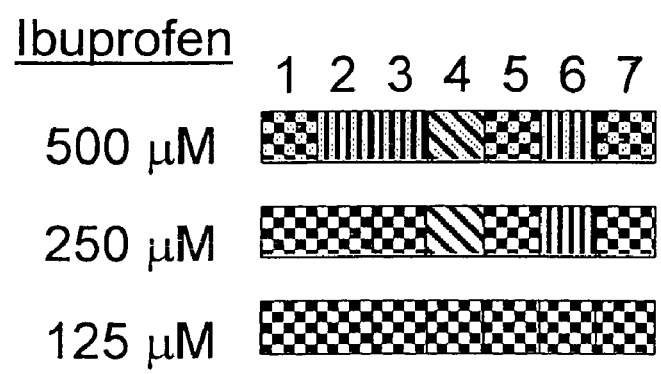

FIG. 3B, is a color-coded representation of the BioMAPs developed from the data shown in A. For each parameter and assay combination, the square is shaded by a checkerboard if the parameter measurement is unchanged (<20% above or below the measurement in the first assay combination (IL-1+TNF-α+INF-γ)) or p>0.05, n=3; slanted lines indicates that the parameter measurement is moderately increased (>20% but <50%); white indicates the parameter measurement is strongly increased (>50%); vertical lines indicates that the parameter measurement is moderated decreased (>20% but <50%); hatched lines indicates that the parameter measurement is strongly decreased (>50% less than the level measured in the first assay combination).

Inhibitors of NFκB, MAP kinases and non-steroidal anti-inflammatory drugs are active compounds in the optimized assay combination described above. FIG. 3A shows results of assaying confluent cultures of HUVEC cells treated with TNF-α (5 ng/ml)+IFN-γ (100 ng/ml)+IL-1 (1 ng/ml) in the presence or absence of (A) 10 μM NHGA, 200 μM PDTC or 9 μM PD098059 or (B) 125-500 μM ibuprofen. Compounds are tested at the highest concentration at which they are soluble, and do not result in cellular toxicity or loss of cells from the plate. After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. A color-coded representation of the BioMAPs developed from the data is shown. For each parameter and assay combination, the square is shaded by a checkerboard if the parameter measurement is unchanged (<20% above or below the measurement in the first assay combination (IL-1+TNF-α+INF-γ)) or p>0.05, n=3; slanted lines indicates that the parameter measurement is moderately increased (>20% but <50%); white indicates the parameter measurement is strongly increased (>50%); vertical lines indicates that the parameter measurement is moderated decreased (>20% but <50%); hatched lines indicates that the parameter measurement is strongly decreased (>50% less than the level measured in the first assay combination).

In the present example, FIG. 3A shows how addition of the NFκB inhibitors nordihydroguaiaretic acid (NHGA) (Brennen, Biochem. Pharmacol., 55:965, 1998) or pyrrolidine dithiocarbamate (PDTC) (Boyle, Circulation, 98, (19 Suppl): II282, 1998) to the optimized assay combination results in altered BioMAPs that are distinct from the altered BioMAPs obtained with the p42/44 MAP kinase inhibitor, PD098059 (Milanini, J. Biol. Chem. 273:18165, 1998). Active compounds that act with a similar mechanism of action as NHGA and PDTC will give a BioMAP that can be distinguished from active compounds that act with a similar mechanism of action as PD098059.

Obtaining BioMAPs from drug compounds tested at different concentrations also expands the usefulness of the database. In the present example, ibuprofen gives visually distinct BioMAPs when tested at 500, 250 and 125 µM, as shown in FIG. 3B, although regression analysis indicates they are highly related (correlation coefficients derived from the primary data range between 0.96-0.99).

Reference BioMAPs from assay combinations that include known drug compounds, agents, or with other specific modifications are developed for inclusion in a database. Biomaps from these assay combinations are developed so as to expand the usefulness of the database. Table 1 shows a list of agents or specific modifications evaluated, including N-acetylcysteine (Faruqui, Am. J. Physiol. 273(2 Pt 2):H817, 1997), the corticosteroids dexamethasone and prednisolone, echinacea, AA861 (Lee, J. Immunol. 158, 3401, 1997), apigenin (Gerritsen, Am. J. Pathol. 147:278, 1995), nordihydroguaiaretic acid (NHGA) (Brennen, Biochem. Pharmacol., 55:965, 1998), phenylarsine oxide (PAO) (Dhawan, Eur. J. Immunol. 27:2172, 1997), pyrrolidine dithiocarbamate (PDTC) (Boyle, Circulation, 98, (19 Suppl):II282, 1998), PPM-18 (Yu, Biochem. J., 328:363, 1997), the non-steroidal anti-inflammatory drug (NSAID) buprofen, SB 203580, PD098059 (Milanini, J. Biol. Chem. 273:18165, 1998), AG126 (Novogrodsky, Science 264, 1319, 1994), and neutralizing anti-TNF-α antibody. Color-coded representations of the resulting BioMAPs are shown. Confluent cultures of HUVEC cells are treated with TNF-α (5 ng/ml)+INF-γ (100 ng/ml)+IL-1 (1 ng/ml) in the presence or absence of agents or buffers at the concentrations indicated in Table 1. Compounds are obtained from commercial sources and prepared in a suitable buffer (water, base media, DMSO, methanol or ethanol). After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. A color-coded representation of the resulting BioMAPs developed from the data is shown. For each parameter and assay combination, the square is colored light gray if the parameter measurement is unchanged (<20% above or below the measurement in the control assay combination (IL-1+TNF-α+INF-γ)) or p>0.05, n=3; white/gray hatched indicates that the parameter measurement is moderately increased (>20% but <50%); white indicates the parameter measurement is strongly increased (>50%); black/gray hatched indicates that the parameter measurement is moderately decreased (>20% but <50%); black indicates that the parameter measurement is strongly decreased (>50% less than the level measured in the first. Control assay combinations for each agent include an appropriate concentration of the diluent buffer.

TABLE 1

REFERENCE BioMAPs.

| Inhibitor Class | UID | Compound | Conc. | Units | Readout Parameters | | | | | | |
|---|---|---|---|---|---|---|---|---|---|---|---|
| | | | | | 1 | 2 | 3 | 4 | 5 | 6 | 7 |
| Antioxidant | 181 | N-acetylcysteine | 5.00 | µM | ■ | ■ | ■ | ■ | ■ | ■ | ■ |
| Antioxidant | 182 | N-acetylcysteine | 2.50 | µM | ■ | ■ | ■ | ■ | ■ | ■ | ■ |
| Antioxidant | 183 | N-acetylcysteine | 1.25 | µM | ■ | ■ | ■ | ■ | ■ | ■ | ▨ |
| Antioxidant | 184 | N-acetylcysteine | 1.25 | µM | ■ | ■ | ■ | ■ | ■ | ■ | ▨ |
| Corticosteroid | 717 | Dexamethazone | 12.50 | µM | ■ | ■ | ■ | ▨ | ■ | □ | ▨ |
| Corticosteroid | 716 | Dexamethazone | 6.25 | µM | ■ | ■ | ■ | ▨ | ■ | □ | ▨ |
| Corticasteroid | 715 | Dexamethazone | 3.10 | µM | ▦ | ▦ | ▦ | ▦ | ▦ | □ | ▨ |
| Corticasteroid | 301 | Dexamethazone | 2.00 | µM | ▦ | ▦ | ▨ | ▨ | ■ | □ | ▨ |
| Corticosteroid | 302 | Dexamethazone | 1.00 | µM | ▦ | ▦ | ▨ | ▨ | ■ | □ | ▨ |
| Corticosteroid | 303 | Dexamethazone | 0.50 | µM | ▦ | ▦ | ▨ | ▦ | ▦ | □ | ▨ |

TABLE 1-continued

REFERENCE BioMAPs.

| Inhibitor Class | UID | Compound | Conc. | Units | Readout Parameters 1 | 2 | 3 | 4 | 5 | 6 | 7 |
|---|---|---|---|---|---|---|---|---|---|---|---|
| Corticosteroid | 241 | Prednisolone | 160.00 | μM | ■ | ■ | ■ | ■ | ■ | □ | ■ |
| Corticosteroid | 242 | Prednisolone | 160.00 | μM | ▦ | ▦ | ▨ | ▨ | ▦ | □ | ▦ |
| Corticosteroid | 243 | Prednisolone | 80.00 | μM | ▦ | ▦ | ▦ | ▦ | ▦ | □ | ▦ |
| Corticosteroid | 244 | Prednisolone | 40.00 | μM | ▦ | ▦ | ▨ | ▦ | ▦ | □ | ▦ |
| Natural Product | 91 | Echinacea | 2.27 | & | ▦ | ▨ | ▦ | □ | ▦ | ▨ | ■ |
| Natural Product | 94 | Echinacea | 2.27 | % | ▦ | ■ | ▦ | □ | ▨ | ▦ | ▨ |
| Natural Product | 92 | Echinacea | 1.13 | % | ▦ | ▦ | ▦ | □ | ▦ | ▦ | ▨ |
| Natural Product | 93 | Echinacea | 0.57 | % | ▦ | ▦ | ▦ | □ | ▦ | ▦ | ▦ |
| NFκB | 4 | AA861 | 20.00 | μM | ▦ | ■ | ■ | ▨ | ND | ■ | ▨ |
| NFκB | 5 | AA861 | 20.00 | μM | ▦ | ▨ | ■ | ▦ | ND | ND | ▦ |
| NFκB | 6 | AA861 | 20.00 | μM | ▦ | ▨ | ▦ | ■ | ▦ | ■ | ■ |
| NFκB | 701 | AA861 | 20.00 | μM | ▦ | ■ | ■ | ▦ | ▦ | ND | ▨ |
| NFκB | 19 | Apigenen | 8.10 | μM | ▦ | ▨ | ■ | ▦ | □ | ■ | ▨ |
| NFκB | 20 | Apigenen | 6.00 | μM | ▦ | ■ | ■ | ▨ | ▦ | ■ | ▦ |
| NFκB | 21 | Apigenen | 5.00 | μM | ▦ | ▦ | ▦ | ▦ | ▨ | ▨ | ▦ |
| NFκB | 202 | Nordihydroguaiaretic acid (NHGA) | 10.00 | μM | ▦ | ■ | ■ | ▦ | ND | ▨ | ▨ |
| NFκB | 203 | Nordihydroguaiaretic acid (NHGA) | 10.00 | μM | ▦ | ■ | ▨ | ▦ | ND | ND | ▦ |
| NFκB | 204 | Nordihydroguaiaretic acid (NHGA) | 10.00 | μM | ▦ | ■ | ▦ | ▦ | ▦ | ■ | ▨ |
| NFκB | 719 | Nordihydroguaiaretic acid (NHGA) | 6.00 | μM | ▦ | ■ | ▦ | ▦ | ▦ | ■ | ▦ |
| NFκB | 205 | Nordihydroguaiaretic acid (NHGA) | 5.00 | μM | ▦ | ▨ | ▨ | ▦ | ▦ | ▦ | ▨ |
| NFκB | 718 | Nordihydroguaiaretic acid (NHGA) | 0.63 | μM | ▨ | ■ | ■ | ▦ | ▦ | ▦ | ■ |
| NFκB | 720 | PAO | 50.00 | μM | ▨ | ■ | ■ | ▦ | ▦ | ■ | ▨ |
| NFκB | 231 | PDTC | 200.00 | μM | ■ | ■ | ■ | ■ | □ | ■ | ■ |

TABLE 1-continued

REFERENCE BioMAPs.

| Inhibitor Class | UID | Compound | Conc. | Units | Readout Parameters | | | | | | |
|---|---|---|---|---|---|---|---|---|---|---|---|
| | | | | | 1 | 2 | 3 | 4 | 5 | 6 | 7 |
| NFκB | 233 | PDTC | 200.00 | μM | | | | | | | |
| NFκB | 234 | PDTC | 200.00 | μM | | | | | | | |
| NFκB | 725 | PDTC | 100.00 | μM | | | | | | ND | |
| NFκB | 726 | PDTC | 100.00 | μM | | | | | | | |
| NFκB | 235 | PDTC | 100.00 | μM | | | | | | | |
| NFκB | 232 | PDTC | 50.00 | μM | | | | | ND | | |
| NFκB | 724 | PDTC | 50.00 | μM | | | | ND | ND | ND | |
| NFκB | 236 | PDTC | 50.00 | μM | | | | | | | |
| NFκB | 728 | PPM-18 | 2.50 | μM | | | | | | | |
| NFκB | 727 | PPM-18 | 2.00 | μM | | | | | | | |
| NFκB | 735 | PPM-18 | 2.00 | μM | | | | | | | |
| NSAID | 131 | Ibuprofen | 500.00 | μM | | | | | | | |
| NSAID | 132 | Ibuprofen | 500.00 | μM | | | | | | | |
| p38 MAPK | 730 | SB 203580 | 80.00 | μM | | | | | | ND | |
| p38 MAPK | 729 | SB 203580 | 40.00 | μM | | | | | | ND | |
| p42/44 MAPK | 221 | PD098059 | 18.70 | μM | | | | | ND | ND | |
| p42/44 MAPK | 222 | PD098059 | 9.30 | μM | | | | | ND | ND | |
| p42/44 MAPK | 223 | PD098059 | 9.30 | μM | | | | | ND | | |
| p42/44 MAPK | 224 | PD098059 | 9.00 | μM | | | | | | | |
| p42/44 MAPK | 723 | PD098059 | 9.00 | μM | | | | | | ND | |
| p42/44 MAPK | 225 | PD098059 | 4.60 | μM | | | | | ND | ND | |
| p42/44 MAPK | 722 | PD098059 | 2.25 | μM | | | | | | ND | |

TABLE 1-continued

REFERENCE BioMAPs.

| Inhibitor Class | UID | Compound | Conc. | Units | Readout Parameters | | | | | | |
|---|---|---|---|---|---|---|---|---|---|---|---|
| | | | | | 1 | 2 | 3 | 4 | 5 | 6 | 7 |
| p42/44 MAPK | 721 | PD098059 | 0.56 | μM | ▨ | ▨ | ■ | ■ | ■ | ND | ▨ |
| Tyr Kinase | 733 | AG126 | 25.00 | μM | ■ | ■ | ■ | ■ | ■ | ■ | ■ |
| Tyr Kinase | 702 | AG126 | 25.00 | μM | ■ | ■ | ■ | ■ | ■ | ■ | ■ |
| Tyr Kinase | 734 | AG126 | 25.00 | μM | ■ | ■ | ■ | ■ | ■ | ■ | ■ |
| Antibody | 712 | Anti-TNF | 5.00 | μg/ml | ■ | ■ | ■ | ▨ | ND | ND | ▨ |
| Antibody | 713 | Anti-TNF | 5.00 | μg/ml | ▨ | ■ | ■ | ▨ | □ | ND | ▨ |
| Antibody | 711 | Anti-TNF | 4.00 | μg/ml | ■ | ▨ | ■ | ▨ | ND | ND | ■ |
| Antibody | 710 | Anti-TNF | 1.67 | μg/ml | ■ | ■ | ■ | ■ | ND | ND | ▨ |
| Antibody | 709 | Anti-TNF | 0.55 | μg/ml | ■ | ■ | ■ | ■ | ND | ND | ■ |
| Antibody | 708 | Anti-TNF | 0.40 | μg/ml | ■ | ■ | ■ | ■ | ND | ND | ■ |
| Antibody | 707 | Anti-TNF | 0.04 | μg/ml | ■ | ■ | ■ | ■ | ND | ND | ■ |
| Antibody | 714 | Anti-TNF-R (Act) | 5.00 | μg/ml | ■ | ■ | ■ | ■ | ND | ND | ■ |
| N/A | 520 | Control | | | ■ | ■ | ■ | ■ | ■ | ■ | ■ |
| N/A | 521 | Control | | | ■ | ■ | ■ | ■ | ■ | ■ | ■ |
| N/A | 522 | Control | | | ■ | ■ | ■ | ■ | ■ | ■ | ■ |
| N/A | 523 | Control | | | ■ | ■ | ■ | ■ | ■ | ■ | ■ |
| N/A | 524 | Control | | | ■ | ■ | ■ | ■ | ND | ■ | ■ |
| N/A | 525 | No IL1 | | | ▨ | ▨ | ■ | ▨ | ▨ | ▨ | ▨ |
| N/A | 526 | No IL1 | | | ▨ | □ | ▨ | ■ | ▨ | □ | ▨ |
| N/A | 527 | No IL1 | | | ▨ | □ | ▨ | ■ | ND | □ | ▨ |
| N/A | 531 | No TNF | | | ▨ | ▨ | ■ | ▨ | ▨ | ▨ | ▨ |
| N/A | 532 | No TNF | | | ▨ | ▨ | ■ | ▨ | ▨ | □ | ▨ |
| N/A | 533 | No TNF | | | ▨ | ■ | ■ | ▨ | □ | ▨ | ▨ |

TABLE 1-continued

REFERENCE BioMAPs.

| Inhibitor Class | UID | Compound | Conc. | Units | Readout Parameters | | | | | | |
|---|---|---|---|---|---|---|---|---|---|---|---|
| | | | | | 1 | 2 | 3 | 4 | 5 | 6 | 7 |
| N/A | 515 | NoIL1IFNγ | | | | | | | | | |
| N/A | 516 | NoIL1IFNγ | | | | | | | | | |
| N/A | 517 | NoIL1IFNγ | | | | | | | | | |
| N/A | 518 | NoIL1IFNγ | | | | | | | | | |
| N/A | 519 | NoIL1IFNγ | | | | | | | ND | | |
| N/A | 510 | NoTNFIFNγ | | | | | | | | | |
| N/A | 511 | NoTNFIFNγ | | | | | | | | | |
| N/A | 512 | NoTNFIFNγ | | | | | | | | | |
| N/A | 513 | NoTNFIFNγ | | | | | | | | | |
| N/A | 514 | NoTNFIFNγ | | | | | | | ND | | |
| N/A | 505 | No IL1TNF | | | | | | | | | |
| N/A | 506 | No IL1TNF | | | | | | | | | |
| N/A | 507 | No IL1TNF | | | | | | | | | |
| N/A | 508 | No IL1TNF | | | | | | | | | |
| N/A | 509 | No IL1TNF | | | | | | | ND | | |
| N/A | 500 | No IL1TNFIFNγ | | | | | | | | | |
| N/A | 501 | No IL1TNFIFNγ | | | | | | | | | |
| N/A | 502 | No IL1TNFIFNγ | | | | | | | | | |
| N/A | 503 | No IL1TNFIFNγ | | | | | | | | | |
| N/A | 504 | No IL1TNFIFNγ | | | | | | | ND | | |

Figure 3C:
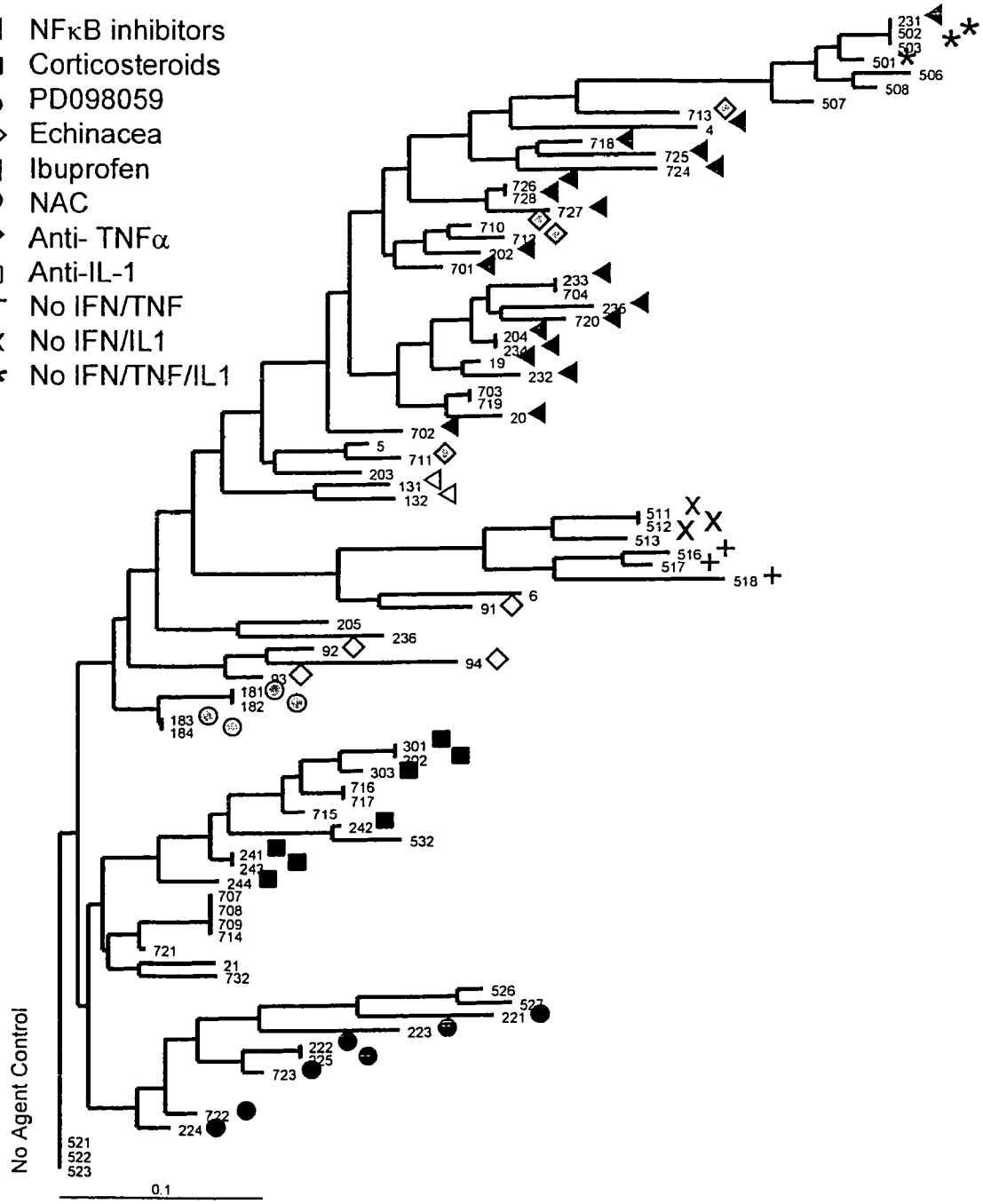

FIG. 3C shows a visual representation of how these reference BioMAPs can be compared by pattern similarity and cluster analysis. Readout patterns are analyzed by hierarchical clustering techniques, and are visualized as a tree diagram in which a) each terminal branch point, represents the readout pattern from one assay combination in one experiment; b) the length of the vertical distance from the upper horizontal line (no change and control patterns) to the termini are related to the extent of difference in the readout pattern from the control environment pattern; and c) the distance along the branches from one terminal pattern value to another reflects the extent of difference between them. Similar patterns are thus clustered together.

Compounds that inhibit the NFκB pathway, such as the 5-lipoxygenase inhibitors AA861 and nordihydroguaiaretid acid (NHGA) (Lee, J. Immunol. 158, 3401, 1997), pyrrolidine dithiocarbamate (PDTC) (Boyle, Circulation 98: (19 Suppl):II282, 1998), PPM-18, a chemically synthesized naphthoquinone derivative (Yu, Biochem. J., 328:363, 1997) and the flavenoid apigenin (Gerritsen, Am. J. Pathol. 147:278, 1995), have similar reference BioMAPs and cluster together. The corticosteroids, dexamethasone and prednisolone also yield a set of related reference BioMAPs that are distinct from those of NFκB pathway inhibitors.

An important feature of BioMAP analysis is how BioMAPs resulting from different concentrations of active agents, although they differ from one another (see FIG. 3C), remain clustered together in the cluster analysis. This can be seen in FIG. 3C where the BioMAPs that result from testing PD098059 at different concentrations remain in the same cluster (indicating-their similarity with one another), although BioMAPs resulting from testing PD098059 at higher concentrations are found in the lower branches of the cluster, indicating higher degree of difference (lower correlation coefficient) from the BioMAPs resulting from no intervention or inactive agents. Thus BioMAP analysis is useful for distinguishing the mode of action of a variety of compounds.

This example demonstrates that the BioMAPs are useful in distinguishing the mode of action of candidate compounds, so as to know whether combinations of candidate compounds act on the same pathway or different pathways, their combined effect on parameter levels and whether they provide synergy or act in an antagonistic way.

These assay combinations are highly useful for testing a large number of compounds or agents with many different or unknown mechanisms of action. This procedure balances the desirability of a screening assay that provides in depth information, with the advantages of an assay that is also amenable for scale-up high throughput screening. The assay combinations described are useful for general screening for compounds with anti-inflammatory or proinflammatory activity. Assay combinations tailored for specific inflammatory diseases are developed by altering the combination of input biologically active agents. For example, specific assay combinations useful for inflammatory diseases that are more Th2-like in nature, such as asthma or allergy should include additional agents, such as IL-4 or IL-13, that are preferably found in those disease conditions, and so forth.

Example 2

BioMAP Assays for Characterizing T Cell Responses—T Cell-Endothelial Cell Co-Cultures The present invention is applied for characterizing patient tissue samples. A set of assay combinations that includes patient samples is utilized to characterize the status of patient samples.

Figure 4:
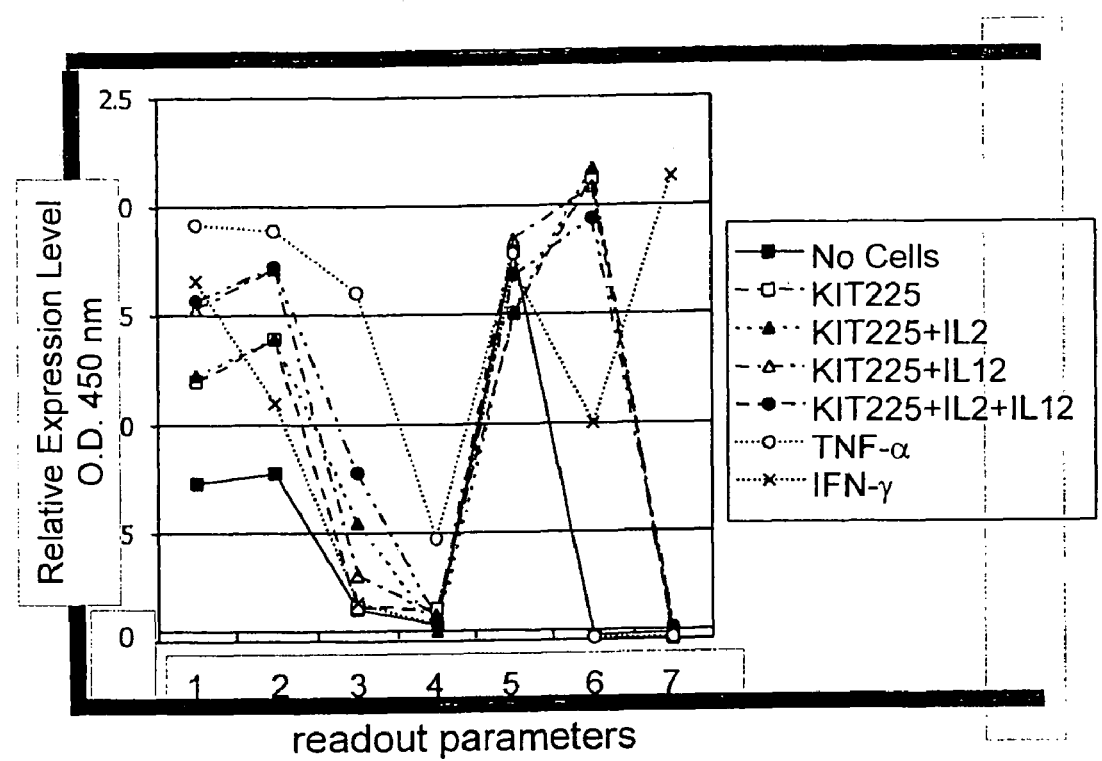
FIG. 4. Assay combinations containing HUVEC and T cell co-cultures. Confluent cultures of HUVEC were incubated with media (No Cells), TNF-α, (5 ng/ml), IFN-γ (100 ng/ml) or KIT255 T cells with and without IL-2 (10 ng/ml) and/or IL-12 (10 ng/ml). After 24 hours cultures were washed and evaluated for the cell surface expression of ICAM-1 (1), VCAM-1 (2), E-selectin (3), IL-8 (4), CD31 (5), HLA-DR (6) and MIG (7) by cell-based ELISA performed as described in FIG. 1. The relative expression of each parameter is shown along the y-axis as average value of the OD measured at 450 nm.BioMAP FIG. 5A-C. Assay combinations for characterizing patient blood samples. Expression of selected readout parameters on selected assay combinations of HUVEC with and without normal blood cells and proinflammatory cytokines. Human peripheral blood buffy coat cells, washed and resuspended to 1/16 volume were added to confluent cultures of HUVEC cells treated with TNF-α (5 ng/ml), IFN-γ (100 ng/ml), IL-1 (1 ng/ml) and or base media. After 24 hours, cultures were washed and evaluated for the presence of the parameters ICAM-1 (1), VCAM-1 (2), E-selectin (3), IL-8 (4), CD31 (5), HLA-DR (6), MIG (7), CD40 (8) or MCP-1 (9) by cell-based ELISA. For this, plates were blocked with 1% Blotto for 1 hr, and treated with primary antibodies (obtained from Pharmingen and Becton Dickinson) at 1 ng/ml for 1 hr. Plates were washed and secondary biotin-conjugated anti-mouse IgG antibody (Jackson Immunoresearch) at 1:2500 was applied for 1 hr. Plates were washed and strepavidin-HRP (Jackson Immunoresearch) was applied for 1 hr. After washing, TMB substrate (Kierkegaard & Perry) was added and color developed. Development was stopped by addition of $H_2SO_4$ and the absorbance at 450 nm (subtracting the background absorbance at 650 nm) with a Molecular Devices plate reader. The relative expression levels of each parameter are indicated by the OD at 450 nm shown along the y-axis. A. Parameter readouts are shown from BioMAPs prepared from assays performed without blood or with blood and with or without one or more of TNFα, IL-1 and/or IFNγ. B. Parameter readouts are shown from BioMAPs prepared from assays performed with (closed symbols) and without (open symbols) blood and (a) IL-1, (b) TNFα, (c) IFNg, (d) IL1+TNF+IFNg, and (e) no added cytokine. C. Visual representation of the data from FIG. 5B. The measurement obtained for each parameter is classified according to its relative change from the value obtained in the indicated assay combination (containing no cytokine; IL-1, TNF-α, IFN-γ or IL-1+TNF-α+INF-γ), and represented by shaded squares. For each parameter and assay combination, the square is shaded by a checkerboard if the parameter measurement is unchanged (<20% above or below the measurement in the first assay combination) or p>0.05, n=3; slanted lines indicates that the parameter measurement is moderately increased (>20% but <50%); white indicates the parameter measurement is strongly increased (>50%); vertical lines indicates that the parameter measurement is moderated decreased (>20% but <50%); hatched lines indicates that the parameter measurement is strongly decreased (>50% less than the level measured in the assay combination without blood cells).

Primary human umbilical vein endothelial cells and the human T cell line, KIT255 are used. Other cells that may replace HUVEC in the screen include primary microvascular endothelial cells or aortic endothelial cells. $2 \times 10^4$ HUVEC/ml were cultured to confluence in EGM-2-(Clonetics). Other media that may replace EGM-2 include EGM (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973; Hoshi, PNAS 81:6413, 1984). One or more of the following are then applied: $10^3$ KIT255 cells, IL-2 (10 ng/ml), IL-12 (10 ng/ml), and or base media. After 24 hours, cultures are washed and evaluated for the presence of the parameters ICAM-1 (1), VCAM-1(2), E-selectin (3), IL-8 (4), CD31 (5), HLA-DR (6) and MIG (7) by cell based ELISA as described in FIG. 1 and shown in FIG. 4. In this figure, analysis performed by cell based ELISA provides readout patterns that combine HUVEC and T cell readouts. FIG. 4 demonstrates that the BioMAPs derived from assay combinations containing KIT255 cells+/−IL-2 and IL-12 can be distinguished. Other cells that may replace KIT255 include human peripheral blood samples including peripheral blood leukocytes, human peripheral blood T cells, human peripheral blood CD3+ cells, and the human T cell lines Jurkat and HUT78. In subsequent panels, one or more of: PHA, IL-6, IL-7, activating antibody to CD3, activating antibody to CD28, IL-1, TNF-α, IFN-γ, IL-4, IL-13 or neutalizing antibodies to IL-1, IL-2, TNF-α, IFN-γ, IL-12 and/or IL-4 are applied. Other markers of interest for adding to the BioMAP include MCP-1, IP-10, cutaneous lymphocyte antigen (CLA), CXCR3, CCR3, TNF-α, IFN-γ, IL-2, IL-4, alpha4beta7, alphaEbeta7, and L-selectin. Analytical methods that distinguish T cells from endothelial cells, such as flow cytometry or image analytical techniques can be employed. A database of BioMAPs is generated from a panel of assay combinations that include anti-inflammatory drug compounds including inhibitors of T cell activation and/or T cell proliferation, calcineurin inhibitors, etc. are screened and BioMAPs are generated that reflect the changes in the markers with the different agents. Such agents are given in The Pharmacologic Basis of Therapeutics. The BioMAPs with the known agents are used to compare to candidate immunomodulatory agents. This allows the recognition of the pathway(s) the candidate test agent acts on, by comparing the changes in the level of the specific markers for known agents affecting known pathways and the changes observed with the candidate test agent. In addition to further add to the utility of the BioMAP, one may include in the database reference BioMAPs generated from assay panels containing cells with genetic constructs that selectively target or modulate specific cellular pathways (e.g. NFAT, calcineurin, NFκB, MAP kinase, etc), or cells that contain known genetic mutations, e.g. Jurkat cell tines that lack Ick, CD45, etc. (Yamasaki, J. Biol. Chem. 272:14787, 1997).

Example 3

BioMAP Assays for Characterizing Patients from Blood Samples

The present invention is useful for monitoring patients for characterizing their inflammatory status.

Figure 5A:
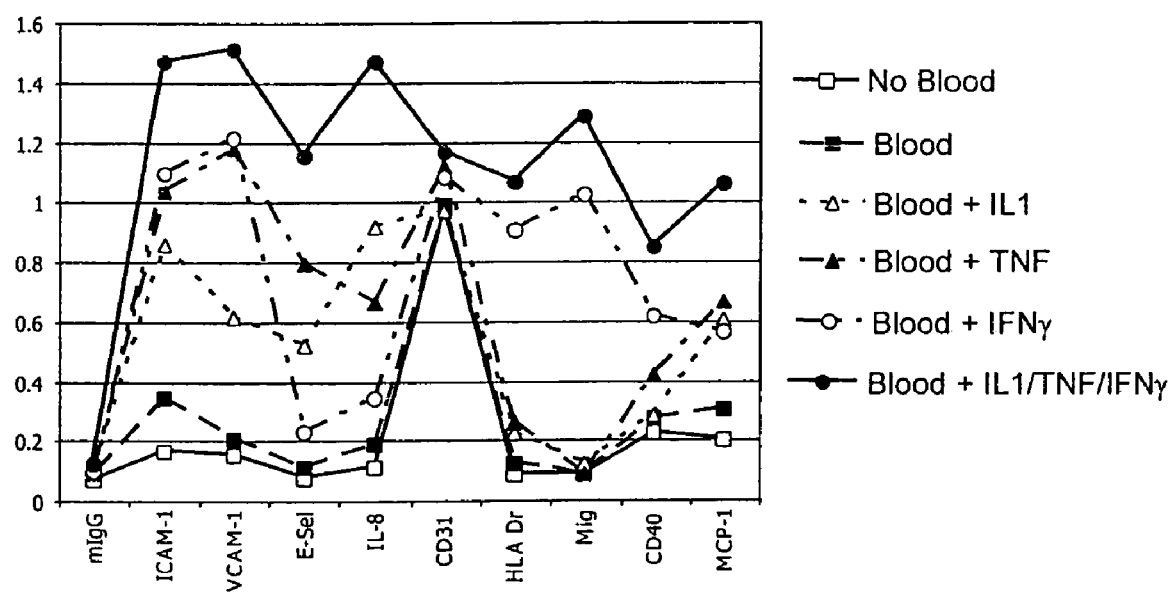
Figure 5B:
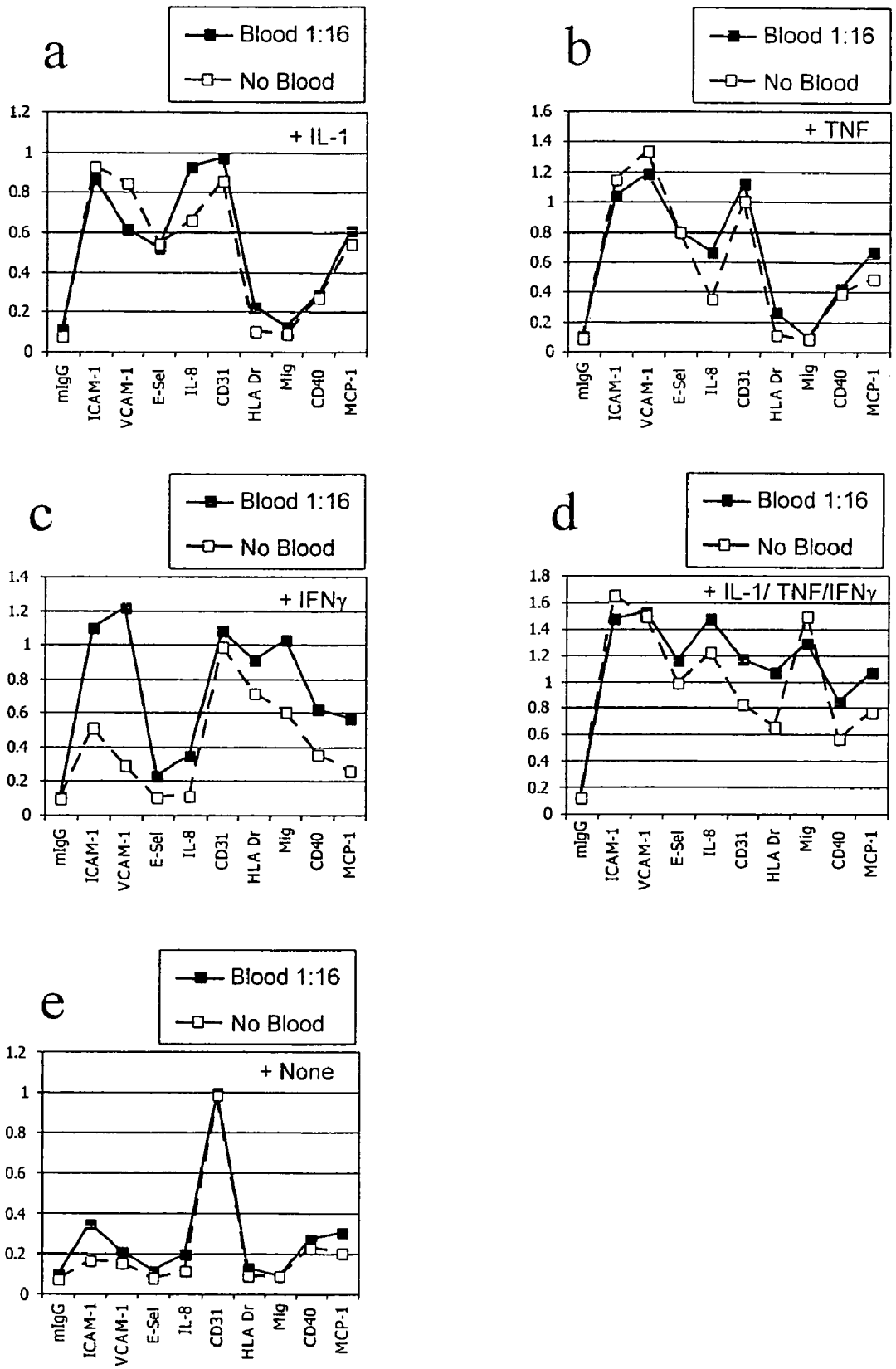
Figure 5C:
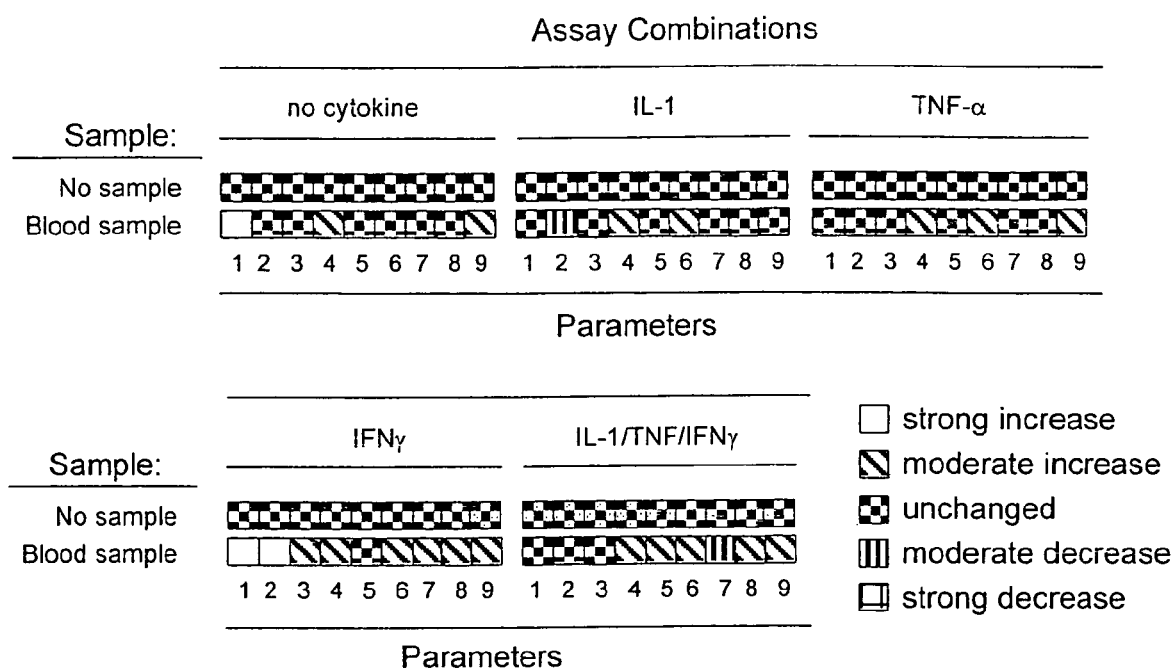

Primary human umbilical vein endothelial cells (HUVEC) are used. Other cells that may replace HUVEC in the screen include primary microvascular endothelial cells, aortic or arteriolar endothelial cells or endothelial cell lines such as EAhy926 or E6-E7 4-5-2G cells or human telomerase reverse transcriptase-expressing endothelial cells (Simmons, J. Immunol., 148:267, 1992; Rhim, Carcinogenesis 19:673, 1998; Yang, J. Biol. Chem. 274:26141, 1999). $2 \times 10^4$ cells/ml are cultured to confluence in base media, EGM-2 (Clonetics). One or more of the following are then applied: human blood cells (prepared from buffy coats obtained from citrated patient blood samples), washed and diluted 1/16), IL1 (1 ng/ml), TNFα (5 ng/ml), IFNγ (100 ng/ml) and or base media. After 24 hours, cultures are washed and evaluated for the presence of the parameters ICAM-1 (1), VCAM-1 (2), E-selectin (3), IL-8 (4), CD31 (5), HLA-DR (6), CD40 (8) and MCP-1 (9) by cell based ELISA. In FIG. 5, analysis performed by cell based ELISA provides readout patterns that combine HUVEC and blood cell readouts. FIG. 5A demonstrates that the readout patterns derived from assay combinations containing endothelial cells and blood cells+/−IL-1, TNFα and IFNγ can be distinguished. FIG. 5B demonstrates that the readout patterns derived from assay combinations containing endothelial cells and either IL-1 (A), TNF (B), IFNγ (C), IL-1+TNF+IFNγ (D) or no exogenous cytokine (E) are distinct with and without addition of blood cells. These assay combinations are useful for monitoring the status of patients and demonstrates that these assay combinations may be employed to monitor the status of inflammatory pathways in patient blood samples.

Other cells that may replace washed human peripheral blood cells are purified or partially purified blood cell subsets such as human peripheral blood T cells, human peripheral blood CD3+ cells, B cells, neutrophils. In subsequent panels, one or more of: PHA, ConA, activating antibody to CD3, bacterial superantigens, activating antibody to CD28, IL-2, IL-4, IL-12, IL-13 or neutalizing antibodies to IL-1, IL-2, TNF-α, IFN-γ, IL-12 and/or IL-4 are applied. Other markers of interest for adding to the BioMAP include IP-10, cutaneous lymphocyte antigen (CLA), CXCR3, CCR3, TNF-α, IFN-γ, IL-2, IL-4, alpha4beta7, alphaEbeta7, and L-selectin. Analytical methods that distinguish T cells from endothelial cells, such as flow cytometry or image analytical techniques can be employed. A database of BioMAPs is generated from a panel of assay combinations that include anti-inflammatory drug compounds including corticosteroids, inhibitors of T cell activation and/or T cell proliferation, and inhibitors of calcineurin, TNF-α, IL-1, etc. are screened and BioMAPs are generated that reflect the changes in the markers with the different agents. Such agents are given in The Pharmacologic Basis of Therapeutics. BioMaps derived from blood samples from normal humans are used to compare BioMAPs derived from samples obtained from patients. In this way the inflammatory status of patients can be assessed. This allows the recognition of the pathway(s) that are active or inactive in the patient cells by comparing the changes in the level of the specific markers for known agents affecting known pathways in normal human cells and the changes observed with the patient cells.

Patient groups for which this would be of interest include patients on immunosuppressive therapy such as transplant patients; and patients with inflammatory or autoimmune disease in treatment with therapies such as non-steroidal anti-inflammatories, methotrexate, cyclosporin, TNFα-antagonists; as well as otherwise immune compromised patients such as patients suffering from HIV infection, cancer, etc.

Example 4

BioMAPs for Characterization of Patient Cells with Genetic Modifications

The present invention is useful for characterizing patients with genetic differences. The present examples describes how the invention allows differentiating and characterization of cells from patients with genetic differences. In this example, Jurkat T cells are employed. Jurkat cells are a human T cell line originally isolated from a patient with leukemia (Schneider, Int. J. Cancer 19:621, 1977). A genetic mutant Jurkat cell line lacking the 13 chain of the TCR has been described (Ohashi, Nature 316:606, 1985). Primary human umbillical vein endothelial cells (HUVEC) are also used. Other cells that may replace HUVEC in the screen include primary microvascular endothelial cells, aortic or arteriolar endothelial cells or endothelial cell lines such as EAhy926 or E6-E7 4-5-2G cells or human telomerase reverse transcriptase-expressing endothelial cells (Simmons, J. Immunol., 148:267, 1992; Rhim, Carcinogenesis 19:673, 1998; Yang, J. Biol. Chem. 274:26141, 1999). $2 \times 10^4$ HUVEC/ml are cultured to confluence in base media, EGM-2 (Clonetics). One or more of the following are then applied: $2 \times 10^4$ Jurkat cells or Jurkat mutants, superantigen (staphylococcal enterotoxin B, 20 ng/ml), IL1 (1 ng/ml), TNFα (5 ng/ml), IFN-γ (100 ng/ml) and or base media. After 24 hours, cultures are washed and evaluated for the presence of the parameters ICAM-1 (1), VCAM-1 (2), E-selectin (3), IL-8 (4), CD31 (5), HLA-DR (6), MIG (7), CD40 (8) and MCP-1 (9) by cell based ELISA.

A database of BioMAPs is generated from a panel of assay combinations that include normal Jurkat T cells in the presence and absence of each biologically active factor; and reference drugs or agents including anti-inflammatory drug compounds including inhibitors of T cell activation and/or T cell proliferation, calcineurin inhibitors, inhibitors of signaling pathways such as NFAT, calcineurin, NFκB, MAP kinases, etc. are screened and BioMAPs generated that show the changes in the markers with the different agents. Many agents are given in The Pharmacologic Basis of Therapeutics. The BioMAPs with the known agents are used to compare to BioMAPs generated from mutant Jurkat cells. This allows the recognition of the pathway(s) altered in the mutant cells, by comparing the changes in the level of the specific markers for known drugs affecting known pathways in normal cells and the changes observed with the mutant cells. BioMAPs prepared with Jurkat T cells lacking the TCRβ can be readily distinguished BioMAPs prepared from normal Jurkat cells.

This application would be useful for characterizing patients that have genetic differences contributing to their susceptibility to disease or responsiveness to drugs.

Example 5

BioMAPs for Characterization of Patient Cells with Genetic Modifications—Genetically Modified Mice The following example demonstrates the utility of the invention in differentiating and catagorizing cells from patients with genetic differences. In this example, lymphocytes isolated from spleens of gene-deficient mice, such as TNFα-deficient mice (TNFα−/−; Marino, PNAS 94:8093, 1997) and primary human umbilical vein endothelial cells (HUVEC) are employed. Other cells that may replace HUVEC in the screen include primary microvascular endothelial cells or aortic endothelial cells. $2 \times 10^4$ HUVEC/ml are cultured to confluence in EGM-2 (Clonetics). Other media that may replace EGM-2 include EGM (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745, 1973;

Hoshi, PNAS 81:6413, 1984). One or more of the following are then applied: $2 \times 10^4$ spleen cells from TNFα–/–mice (Marino, PNAS 94:8093, 1997) or normal mice, superantigen (staphylococcal enterotoxin B, 20 ng/ml), IL1 (1 ng/ml), TNFα (5 ng/ml), IFN-γ (100 ng/ml), and or base media. After 24 hours, cultures are washed and evaluated for the presence of the parameters ICAM-1 (1), VCAM-1 (2), E-selectin (3), IL-8 (4), CD31 (5), HLA-DR (6), CD40 (8) and MCP-1 (9) by cell based ELISA.

A database of BioMAPs is generated from a panel of assay combinations that include normal murine spleen cell's and HUVEC in the presence and absence of each biologically active factor; and reference drugs or agents including anti-inflammatory drug compounds including inhibitors of T cell activation and/or T cell proliferation, calcineurin inhibitors, inhibitors of signaling pathways such as NFAT, calcineurin, NFκB, MAP kinases, etc. are screened and BioMAPs generated that show the changes in the markers with the different agents. Many agents are given in The Pharmacologic Basis of Therapeutics. The BioMAPs with the known agents are used to compare to BioMAPs generated from mutant mouse cells. This allows the recognition of the pathway(s) that are altered in the mutant mouse cells, by comparing the changes in the level of the specific markers for known drugs affecting known pathways from normal mice and the changes observed with mutant mouse cells.

In subsequent panels, one or more of: PHA, IL-6, IL-7, activating antibody to CD3, activating antibody to CD28, IL-2, IL-12, IFN-γ, IL-4, IL-13 or neutralizing antibodies to IL-1, IL-2, TNF-α, IFN-γ, IL-12 and/or IL-4 are applied.

This application would be useful for characterizing patients that have genetic differences contributing to their susceptibility to disease or responsiveness to drugs.

Example 6

BioMAPs for Characterization of Patients with Cancer

Cancers vary widely in their etiologies and responsiveness to therapy, even for patients with cancers of the same type and stage. While there are many mechanisms that contribute to the cancer phenotype, all cancers result in part from genetic alterations that result in loss of the control of cell growth. Because so many factors act to promote and regulate cell growth, the mechanisms responsible in individual patients and, therefore, the appropriate treatments for individual patients can differ. Evaluating patient tumor cells in BioMAP assays is therefore useful for characterizing patients. In this example, the human breast cell lines MCF-7, UACC-812 and HCC38 are used to illustrate the application. MCF-7 expresses the estrogen receptor; UACC-812 is negative for the estrogen receptor, but positive for Her-2/neu antigen, and MCC38 does not express either. $2 \times 10^5$ cells/ml are cultured in RPMI medium 10% FBS. Other media that may replace RPMI include Dulbecco's Modified Eagle's Medium containing 20% FBS. Following overnight serum starvation one or more the following are then applied for 24 hours: estrogen ($10^{-7}$ M), antibody to Her-2/neu, epidermal growth factor (10 ng/ml) and FGF (2 ng/ml). In subsequent panels one or more of IGF-I (5 nM), TNF-α (100 ng/ml), IFN-γ (200 U/ml), IL-13 (30 ng/ml), TGF-β (10 ng/ml), IL-1β (10 ng/ml) and IL-6; and/or neutralizing antibodies to autocrine factors, IL-1, TGF-β or the receptor IGF-R I, are added to the initial three factors or may replace one of the three factors. Standard concentrations of agents are employed as described in the literature (Jackson, JBC 273:9994, 1998; He, PNAS 97:5768, 2000). BioMAPs are generated for the parameters ICAM-1 (CD54), EGF-R, MCP-1, E-cadherin, HLA-DR (CD74), CD44, carcinoembryonic antigen (CEA, CD66e) and $α_5β_1$. Other markers of interest for adding to the BioMAP include HLA-I, poly-Ig-receptor, IL-8, CD40, CA-19-9, CD95, $α_2β_1$, $α_3β_1$, $α_6β_1$, $α_6β_4$, $α_v$, laminin 5, urokinase-type plasminogen activator receptor (uPAR), and TNFR-I. Parameters of interest also include parameters indicative of cell damage and apoptosis including released cytoplasmic lactate dehydrogenase (LDH) or mitochondrial cytochrome c, appearance of APO2.7 epitope or active caspase-3 (Koester, Cytometry, 33:324, 1998; Zhang, J. Immunol., 157:3980, 1996; Bussing, Cytometry 37:133, 1999). Parameters indicative of cell proliferation are also of interest and include Ki-67 and PCNA (Landberg, Cytometry, 13:230, 1992).

BioMAPs generated for MCF-7, UACC-812 and HCC38 are characteristic of the pathways active in each cell type and distinguish the responsiveness of cells to estrogen and/or Her-2/neu ligands and other factors.

A database of BioMAPs is generated from a panel of assay combinations that include a panel of breast cancer cell lines with the differentiation-inducing agent calcitriol, and known anti-cancer agents, anti-estrogens, DNA synthesis inhibitors, nucleoside analogs, topoisomerase inhibitors, and microtubule function inhibitors are screened and a BioMAP generated that shows the changes in the markers with the different anti-cancer agents. Such compounds are given in Weinstein, 1997, and The Pharmacologic Basis of Therapeutics. The BioMAPs with cell lines are used to compare to patient tumor samples. This allows the recognition of the pathway(s) active in the patient tumor cells, by comparing the changes in the level of the specific markers foreknown drugs affecting known pathways and the changes observed with the patient cells.

This application would be useful in characterizing patient samples vis-a-vis responsiveness either to particular therapies, such as anti-estrogen therapy (e.g. tamoxifen) or therapy directed towards the Her-2/neu pathway (e.g. Herceptin) .BioMAP Although the invention has been described with reference to the above examples, it will be understood that modifications and variations are encompassed within the spirit and scope of the invention. Accordingly, the invention is limited only by the following claims.

What is claimed is:

1. A method of preparing a biomap for the classification of a patient sample according to the physiological status of cells or constituents present in the sample, the method comprising:

contacting a patient sample in a test cell culture with at least two factors acting on said cells in an amount and incubating for a time sufficient to induce a plurality of pathways active in said cell culture;

recording changes in at least two parameter readouts associated with said plurality of pathways;

deriving a biomap from said changes in parameter readouts, wherein said biomap comprises data normalized to be a ratio of test to control data on the sample type under control conditions; and analyzing said biomap by a pattern recognition algorithm to quantify relatedness of said biomap to reference biomaps that include one or more of biomaps of normal cells, cells from similarly diseased tissue, or from cell lines with responses induced by assay combinations involving known pathway stimuli or inhibitors, wherein the presence or absence of relatedness to said reference biomaps provides a characterization of the physiological status of cells or constituents present in the sample.

2. The method according to claim 1, wherein said cell culture comprises patient cells, non-patient indicator cells, or a mixture thereof.

3. The method according to claim 1, wherein said patient sample is distributed in a panel of cell culture assay combinations, wherein at least one of said assay combinations is a control cell culture differing in at least one component from said test cell culture; wherein said component can be a factor, a biologically active agent or other environmental condition.

4. A method for characterization of a cellular patient sample as to the ability of cells in the sample to respond to a therapeutic agent, the method comprising:
    contacting the therapeutic agent with a patient sample comprising cells in a test cell culture with at least two factors acting on said cells in an amount and incubating for a time sufficient to induce a plurality of pathways active in said cell culture;
    recording changes in at least four parameter readouts associated with said plurality of pathways as a result of introduction of the therapeutic agent;
    deriving a biomap from said changes in parameter readouts, wherein said biomap comprises data normalized to be a ratio of test to control data on the sample under control conditions in the absence of the therapeutic agent; and
    analyzing said biomap by a pattern recognition algorithm to quantify relatedness of said biomap to reference biomaps that include one or more of biomaps of normal cells, cells from similarly diseased tissue, or from cell lines with responses induced by assay combinations involving known pathway stimuli or inhibitors, wherein the presence or absence of relatedness to said reference biomaps provides a characterization of the signaling pathway responsiveness of said patient sample to said therapeutic agent.

5. The method according to claim 4, wherein said patient sample comprises two or more distinct types of cells.

6. The method according to claim 5, wherein said distinct types of cells are selected from the group consisting of endothelial cells, tumor cells, lymphocytes, monocytes, epithelial cells, neoplastic cells and mast cells.

7. The method according to claim 5, wherein cells in said patient sample are separated according to phenotype prior to said contacting step.

8. The method according to claim 1, further comprising the step of analyzing said cellular patient sample for the presence of nucleic acid polymorphisms.

9. The method according to claim 4, further comprising the step of correlating said biomap with patient history and clinical diagnosis.

10. The method of claim 4, wherein said method further comprises contacting the patient sample with a combination of therapeutic agents.

11. A method for characterization of an acellular patient sample for the activity of constituents in the sample, the method comprising:
    contacting the acellular patient sample with cells in a test cell culture comprising at least two factors acting on said cells in an amount and incubated for a time sufficient to induce a plurality of pathways active in said cell culture;
    recording changes in at least four parameter readouts associated with said plurality of pathways as a result of introduction of the acellular patient sample;
    deriving a biomap from said changes in parameter readouts, wherein said biomap comprises data normalized to be a ratio of test to control data on the sample under control conditions in the absence of the acellular patient sample; and
    analyzing said biomap by a pattern recognition algorithm to quantify relatedness of said biomap to reference biomaps that include one or more of biomaps of normal cells, cells from similarly diseased tissue, or from cell lines with responses induced by assay combinations involving known pathway stimuli or inhibitors, wherein the presence or absence of relatedness to said reference biomaps provides a characterization of the signaling pathway responsiveness of the cell culture to the acellular patient sample.

* * * * *